(12) United States Patent
Kurnadi et al.

(10) Patent No.: US 9,588,064 B2
(45) Date of Patent: Mar. 7, 2017

(54) CHARGED PARTICLE TOMOGRAPHY WITH IMPROVED MOMENTUM ESTIMATION

(71) Applicant: Decision Sciences International Corporation, Poway, CA (US)

(72) Inventors: Priscilla Kurnadi, San Diego, CA (US); Thomas Taylor, St. Johns, FL (US); Sean Simon, Vista, CA (US)

(73) Assignee: Decision Sciences International Corporation, Poway, CA (US)

( * ) Notice: Subject to any disclaimer, the term of this patent is extended or adjusted under 35 U.S.C. 154(b) by 0 days.

(21) Appl. No.: 14/874,305

(22) Filed: Oct. 2, 2015

(65) Prior Publication Data

US 2016/0097729 A1    Apr. 7, 2016

Related U.S. Application Data

(60) Provisional application No. 62/060,993, filed on Oct. 7, 2014, provisional application No. 62/076,092, filed on Nov. 6, 2014.

(51) Int. Cl.
*G01V 5/00* (2006.01)
*G01N 23/20* (2006.01)
*G01N 23/04* (2006.01)

(52) U.S. Cl.
CPC ........... *G01N 23/046* (2013.01); *G01N 23/20* (2013.01)

(58) Field of Classification Search
CPC .. G01V 5/0025; G01V 5/0075; G01V 5/0016; G01V 5/005; G01V 5/00;
(Continued)

(56) References Cited

U.S. PATENT DOCUMENTS 6,484,051 B1 * 11/2002 Daniel .................. G01N 23/20
250/363.03
7,714,297 B2 * 5/2010 Morris .................. G01N 23/20
250/393

(Continued)

FOREIGN PATENT DOCUMENTS

WO    2008/140559 A2    11/2008
WO    2012/167381 A1    12/2012

OTHER PUBLICATIONS

Hohlmann, M., et al, "GEANT4 Simulation of a Cosmic Ray Muon Tomography System With Micro-Pattern Gas Detectors for the Detection of High-Z Materials," IEEE Transactions on Nuclear Science, 56(3):1356-1363, Jun. 2009.

(Continued)

*Primary Examiner* — David A Vanore
(74) *Attorney, Agent, or Firm* — Perkins Coie LLP

(57) ABSTRACT

Methods, devices, systems and computer program products produce and utilize improved momentum estimates for charged particles such as electrons and muons. One method for measuring momentum includes obtaining charged particle tomographic data at one or more charged particle position detectors corresponding to scattering angles of charged particles that pass through an object volume. The distribution of scattering angles associated with the charged particles is determined using measured data collected from the position detectors, based on deviations of local trajectories of the charged particles in one or more planes relative to a reference trajectory. The method also includes determining a length of the scattering material based on the characteristics of the position detectors and the charged particles' angle of incidence on the position detectors, and obtaining charged particle momentum estimates based on
(Continued)

the determined distribution of scattering angles and the length of the scattering material.

30 Claims, 19 Drawing Sheets

(58) Field of Classification Search
CPC .... G01N 23/20; G01N 23/201; G01N 23/046;
G01N 23/20008; G01N 23/207; G01T
1/18; G01T 1/167; G01T 1/2985; G01T
3/00; A61B 6/4258; A61B 6/032; A61B
6/037; A61B 6/12; A61B 6/4266; A61B
6/469; A61B 6/508; A61B 6/5205; A61B
6/5235; A61B 6/542
USPC .......... 250/307, 306, 358.1, 363.03, 370.08,
250/370.09, 251, 305, 308, 363.07, 370.1,
250/390.01, 393, 394, 397
See application file for complete search history.

(56) References Cited

U.S. PATENT DOCUMENTS

| | | | | |
|---|---|---|---|---|
| 7,838,841 B2* | 11/2010 | Morris | ............... | G01N 23/20 250/370.1 |
| 8,247,767 B2* | 8/2012 | Morris | ............... | G01N 23/20 250/307 |
| 8,288,721 B2* | 10/2012 | Morris | ............... | G01T 1/18 250/251 |
| 8,384,036 B2* | 2/2013 | Conti | ............... | G01T 1/2985 250/363.03 |
| 8,513,601 B2* | 8/2013 | Morris | ............... | G01N 23/20 250/307 |
| 8,536,527 B2* | 9/2013 | Morris | ............... | G01N 23/046 250/306 |
| 8,552,370 B2* | 10/2013 | Schultz | ............... | G01N 23/20 250/306 |
| 8,751,168 B2* | 6/2014 | Billinge | ............... | G01N 23/207 702/128 |
| 2008/0228418 A1 | 9/2008 | Green | | |
| 2008/0265156 A1* | 10/2008 | Morris | ............... | G01N 23/20 250/305 |
| 2008/0315091 A1* | 12/2008 | Morris | ............... | G01T 1/18 250/307 |
| 2010/0032564 A1* | 2/2010 | Morris | ............... | G01N 23/20 250/307 |
| 2011/0248163 A1* | 10/2011 | Morris | ............... | G01N 23/046 250/307 |
| 2013/0238291 A1 | 9/2013 | Schultz et al. | | |
| 2015/0212014 A1* | 7/2015 | Sossong | ............... | G01V 5/0016 250/394 |
| 2015/0246244 A1* | 9/2015 | Sossong | ............... | A61N 5/1071 600/427 |
| 2015/0287237 A1* | 10/2015 | Bai | ............... | G01V 5/0016 382/131 |
| 2016/0097729 A1* | 4/2016 | Kurnadi | ............... | G01N 23/20 250/307 |
| 2016/0104290 A1* | 4/2016 | Patnaik | ............... | G06K 9/2054 382/173 |

OTHER PUBLICATIONS

International Search Report and Written Opinion mailed on Dec. 22, 2015 for International Application No. PCT/US2015/053877, filed on Oct. 2, 2015 (10 pages).

Pesente, S., et al., "First results on material identification and imaging with a large-volume muon tomography prototype," Nuclear Instruments and Methods in Physics Research Section A, 604(3):738-746, Jun. 2009.

Schultz, L.J., et al., "Statistical Reconstruction for Cosmic Ray Muon Tomography," IEEE Transactions on Image Processing, 16(8):1985-1993, Aug. 2007.

\* cited by examiner

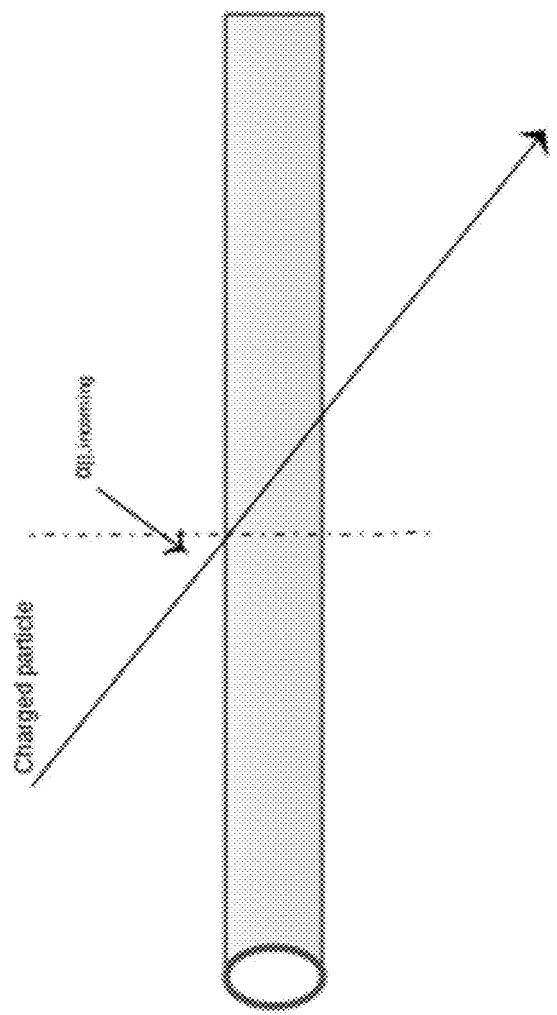
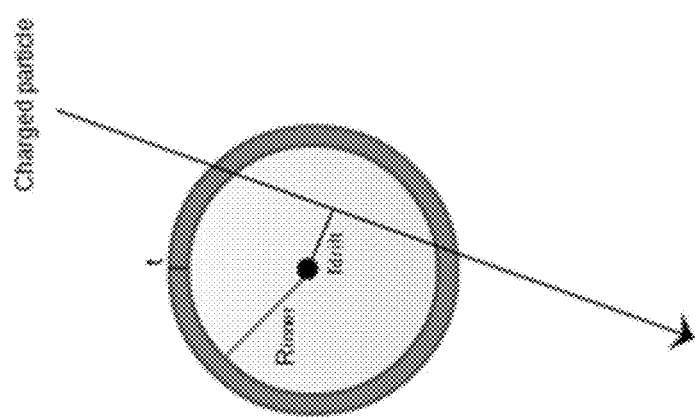
FIG. 8(a)
FIG. 8(b)

CHARGED PARTICLE TOMOGRAPHY WITH IMPROVED MOMENTUM ESTIMATION

CROSS REFERENCE TO RELATED APPLICATIONS

This patent document claims the benefit of priority of U.S. Provisional Patent Application No. 62/060,993, filed on Oct. 7, 2014, and U.S. Provisional Patent Application No. 62/076,092, filed on Nov. 6, 2014. The entire content of the before-mentioned patent applications is incorporated by reference as part of the disclosure of this document.

TECHNICAL FIELD

The subject matter of this patent document relates to particle detection, analysis, control and, more particularly but not exclusively, to methods and systems for reconstructing the trajectory of a charged particle, such as a cosmic ray muon, passing through the charged particle detection system.

BACKGROUND

Charged particle tomography techniques, such as those that rely on cosmic ray muons, generate three-dimensional images of volumes using information contained in the Coulomb scattering of the particles. Since muons are capable of deeper penetration into the object than X-rays, muon tomography can penetrate larger radiation lengths of materials to produce images through much thicker material (e.g., with larger radiation lengths) than X-ray tomography (e.g., CT scans). Applications of tomography techniques include detection of nuclear material in, for example, road transport vehicles and cargo containers, characterization of nuclear waste, monitoring of potential underground sites used for carbon sequestration, prediction of volcanic eruptions, medical imaging and other imaging and detection applications.

Tomography techniques most commonly rely on either transmission radiography or scattering tomography. With scattering tomography, both incoming and outgoing trajectories for each particle are reconstructed by measuring the deviation in trajectory of the charged particle (e.g., muons and electrons), as measured by position detectors, through the tomographic volume. However, knowledge of the particle's momentum can improve the material density estimates that are obtained from reconstruction.

SUMMARY

This patent document discloses designs and implementations of charged particle tomography systems and techniques that produce and utilize improved estimates of the charged particles' momentum.

One aspect of the disclosed technology relates to a method for measuring momentum of charged particles from charged particle tomographic data. The method includes obtaining charged particle tomographic data corresponding to scattering angles of charged particles passing through an object volume at one or more charged particle position detectors, and determining a distribution of scattering angles associated with the charged particles, using measured data collected from the one or more position detectors, based on deviations of local trajectories of the charged particles in one or more planes relative to a reference trajectory. The method also includes determining a length of the scattering material based on the characteristics of the one or more position detectors and the charged particles' angle of incidence on the one or more position detectors, and obtaining charged particle momentum estimates based on the determined distribution of scattering angles and the length of the scattering material.

In one exemplary embodiment, the charged particle momentum estimates are used to determine a reconstructed object volume scattering density using the scattering angles. In another exemplary embodiment, the reference trajectory is an average of all local trajectories obtained from data collected from at least two layers of the position detectors. In still another exemplary embodiment, the above method further includes combining multiple local trajectories to form a non-linear particle path through multiple layers of the position detectors.

According to another exemplary embodiment, the one or more position detectors include a drift tube. In one exemplary embodiment, a local trajectory of the charged particles is at an arbitrary direction in a 3-dimensional coordinate system, and the one or more planes include a plane in the 3-dimensional coordinate system. In another exemplary embodiment, the distribution of scattering angles is determined based on a distribution, $\sigma_\theta^{plane}$, of scattering angles in a plane that is related to a three-dimensional scattering angle distribution, $\sigma_\theta^{3D}$, based on the following relationship: $\sigma_\theta^{3D} = \sqrt{2}\sigma_\theta^{plane}$. In still another exemplary embodiment, the distribution of scattering angles is determined based on the distribution of the local trajectories as the root mean square (RMS) of all the scattering angles for a given charged particle.

In yet another exemplary embodiment, the one or more position detectors include a drift tube and the characteristics of the one or more position detectors include an inner radius of the drift tube and a wall thickness of the drift tube. In one exemplary embodiment, determining the length of the scattering material is further based on the charged particle(s) incident angle projected along a direction of the drift tube's length. In another exemplary embodiment, the above method further includes outputting the reconstructed object volume scattering density for presentation on a display.

Another aspect of the disclosed technology relates to a computer program product, embodied on a non-transitory computer readable medium. The computer program product includes program code for obtaining charged particle tomographic data corresponding to scattering angles of charged particles passing through an object volume at one or more charged particle position detectors, and program code for determining a distribution of scattering angles associated with the charged particles, using measured data collected from the one or more position detectors, based on deviations of local trajectories of the charged particles in one or more planes relative to a reference trajectory. The computer program product also includes program code for determining a length of the scattering material based on the characteristics of the one or more position detectors and the charged particles' angle of incidence on the one or more position detectors, and program code for obtaining charged particle momentum estimates based on the determined distribution of scattering angles and the length of the scattering material.

Another aspect of the disclosed technology relates to a device that includes a processor comprising electronic circuits, and a memory comprising processor executable code, the processor executable code, when executed by the process configures the device to obtain charged particle tomographic data corresponding to scattering angles of charged particles passing through an object volume at one or more charged particle position detectors, and to determine a distribution of scattering angles associated with the charged particles, using measured data collected from the one or more position detectors, based on deviations of local trajectories of the charged particles in one or more planes relative to a reference trajectory. the processor executable code, when executed by the process configures the device to determine a length of the scattering material based on the characteristics of the one or more position detectors and the charged particles' angle of incidence on the one or more position detectors, and to obtain charged particle momentum estimates based on the determined distribution of scattering angles and the length of the scattering material.

Another aspect of the disclosed technology relates to a system for measuring momentum of charged particles from charged particle tomographic data. Such a system includes a first set of position detector located on a first side of an object volume to measure positions and angles of incident charged particles towards the object volume, and a second set of position sensitive detectors located on a second side of the object volume to measure positions and angles of outgoing charged particles exiting the object volume. The system also includes a signal processing unit coupled to the first set of position detectors and to the second set of position detectors to receive data of measured signals from the first set of position detectors and measured signals from the second set of position detectors, the signal processing unit to determine a distribution of scattering angles associated with the charged particles, using measured data collected from the one or more position detectors, based on deviations of local trajectories of the charged particles in one or more planes relative to a reference trajectory, and determine a length of the scattering material based on the characteristics of the first or the second set of position detectors and the charged particles' angle of incidence on the first or the second set of position detectors. The signal processing unit further obtains charged particle momentum estimates based on the determined distribution of scattering angles and the length of the scattering material.

In one exemplary embodiment, the signal processing unit further determines a reconstructed object volume scattering density based on the charged particle momentum estimates and the scattering angles. In one exemplary configuration, the system also includes a display coupled to the signal processing unit to receive and display data representing the reconstructed object volume scattering density. In another exemplary embodiment, the reference trajectory is an average of all local trajectories obtained from data collected from at least two layers of the position detectors. In another exemplary embodiment, the processing unit further combines multiple local trajectories to form a non-linear particle path through multiple layers of the position detectors.

According to yet another exemplary embodiment, the first or the second set of position detectors include a drift tube. In one exemplary embodiment, a local trajectory of the charged particles is at an arbitrary direction in a 3-dimensional coordinate system, and the one or more planes include a plane in the 3-dimensional coordinate system. In another exemplary embodiment, the processing unit determines the distribution of scattering angles based on a distribution, $\sigma_\theta^{plane}$, of scattering angles in a plane that is related to a three-dimensional scattering angle distribution, $\sigma_\theta^{3D}$, based on the following relationship: $\sigma_\theta^{3D} = \sqrt{2}\sigma_\theta^{plane}$.

In another exemplary embodiment, the processing unit determines the distribution of scattering angles based on the distribution of the local trajectories as the root mean square (RMS) of all the scattering angles for a given charged particle. In yet another exemplary embodiment, the first or the second set of position detectors include a drift tube and the characteristics of the first or the second set of position detectors include an inner radius of the drift tube and a wall thickness of the drift tube. In another exemplary embodiment, the processing unit determines the length of the scattering material based on the charged particle(s) incident angle projected along a direction of the drift tube's length.

The above and other features and their embodiments or implementations are described in greater detail in the drawings, the description and the claims.

BRIEF DESCRIPTION OF THE DRAWINGS

FIG. 8(a) is a simplified diagram of a charged particle's pathlength through a drift tube in the plane perpendicular to the direction of the tube length orientation.

FIG. 8(b) is another simplified diagram that shows a charged particle's pathlength through a drift tube in the plane parallel to the direction of drift tube length orientation.

DETAILED DESCRIPTION

The technical features described in this document improve on existing charged particle detection systems that detect charged particles passing through a volume. A charged particle detection system can, for example, include an object holding area for placing an object to be inspected, a first set of position sensitive charged particle detectors located on a first side of the object holding area to measure positions and angles of incident charged particles that travel towards the object holding area. The charged particle detection system can also include a second set of position sensitive charged particle detectors located on a second side of the object holding area opposite to the first side to measure positions and angles of outgoing charged particles that exit the object holding area. It should be noted that the word opposite in the context of this document does not require that the detectors be positioned at the exact opposite sides of the object holding area but rather the word opposite in this context can include placement of the detectors in the path of the charged particle such that the trajectory of the charged particle crosses the first detector, the object holding area and the second detector. Such a system can also include a signal processing unit, which may include a microprocessor to receive data associated with the measured signals corresponding to the incoming charged particles from the first set of position sensitive charged particle detectors and those associated with the outgoing charged particles from the second set of position sensitive charged particle detectors. As an example, each of the first and second sets of particle detectors can be implemented to include drift tubes arranged to allow at least three charged particle positional measurements in a first direction and at least three charged particle positional measurements in a second direction different from the first direction. Such a detection system analyzes scattering behaviors of the charged particles due to their interactions with the object within the object holding area. Such analysis can, for example, include processing of the measured incoming and outgoing positions and angles of the charged particles to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive charged particle detector can be implemented in various configurations, including drift cells such as drift tubes filled with a gas that can be ionized by the charged particles. Such a system can be used to utilize natural cosmic ray muons as the source of muons, as well as other charged particles, for detecting one or more objects in the object holding area.

Figure 1:
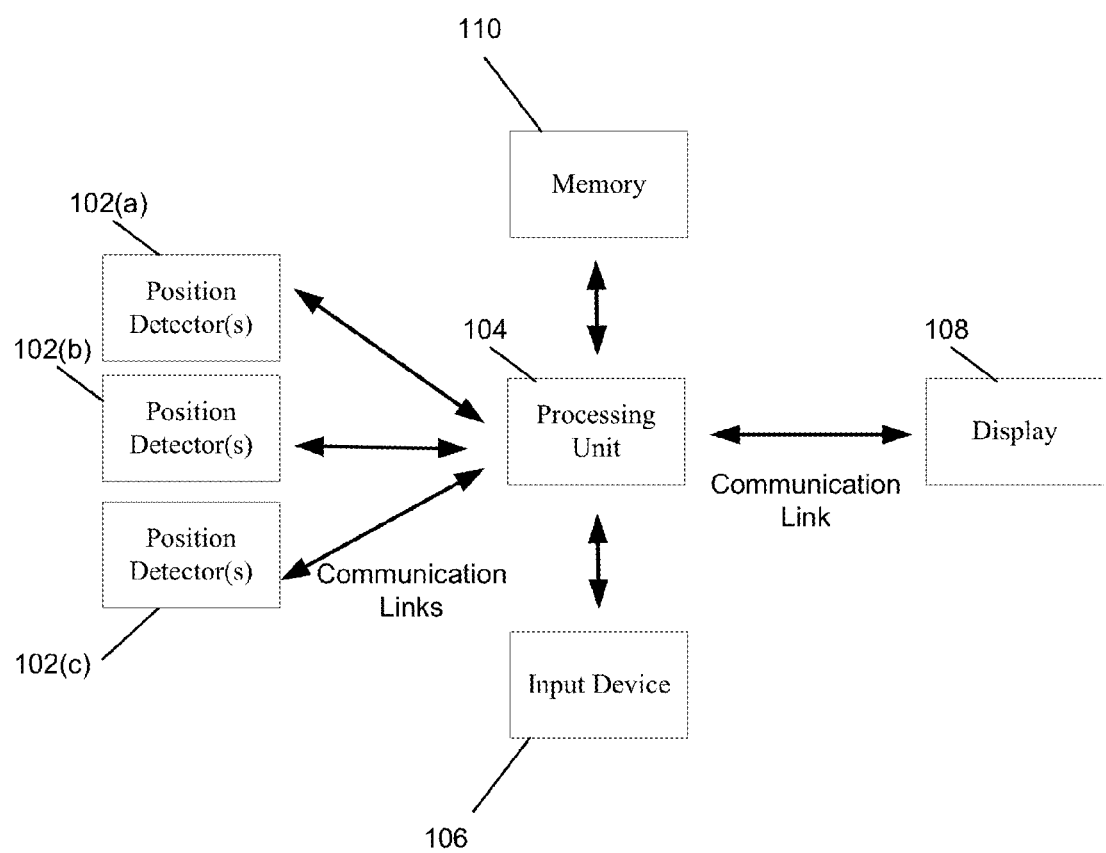
FIG. 1 illustrates a block diagram of charged particle detection system in accordance with an exemplary embodiment.

FIG. 1 illustrates a block diagram of charged particle detection system in accordance with an exemplary embodiment. The system includes a plurality of charged particle detector sets 102(a) to 102(c) that are coupled to a processing unit 104. Each of the charged particle detector sets 102(a) to 102(c) can include one or more drift tubes that are filled with a gas that interacts with the charged particles as the particles traverse through the drift tubes. The detector sets 102(a) to 102(c) can also include the appropriate components and electronics that can be used to produce signals associated with the detected charged particles. The processing unit 104 can be a microprocessor or controller that is in communication with a memory 110 that includes the appropriate program code that can be executed by the processing unit 104 to enable retrieval (or acquisition) of data associated with charged particle measurements, perform various computations as needed to process the received data, and to output data corresponding to the processed data to, for example, a display 108. The memory 110 can be implemented separately or integrated with the processing unit 104, and may be used to store data, program code, and other information. The input device 106 is coupled to the processing unit 104 and provides an input mechanism to allow a user to provide data and commands to the processing unit 104. Examples of the input device include, but are not limited to, a keyboard, a mouse, a microphone, and a track ball. In some implementations the input device 106 may be implemented, at least in-part, as part of the display 108. For example, the input device 106 and the display 104 may collectively form a touch-screen device.

It is understood some of the components of the disclosed particle detection systems, such as the processing unit 104 of FIG. 1, can be implemented individually, or collectively, in devices comprised of various hardware and/or software modules and components, or as a combination of hardware and software. For instance, a hardware implementation can include discrete analog and/or digital components that are, for example, integrated as part of a printed circuit board. Alternatively, or additionally, such components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities.

Figure 2:
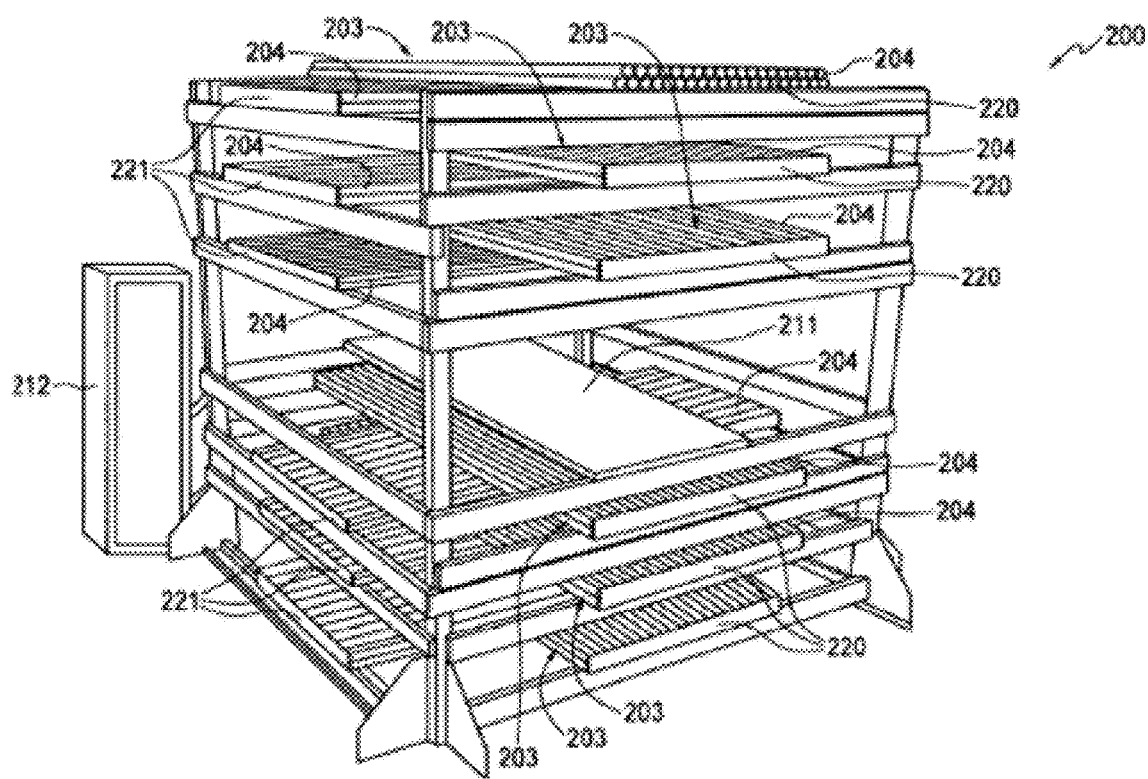
FIG. 2 illustrates an example of a charged particle detector 200 having sets of position sensitive detectors.

FIG. 2 illustrates an example of a charged particle detector 200 having sets of position sensitive detectors 203. Three sets of the position sensitive detectors 203 are arranged above the sample holder plane 211 and three sets of position sensitive detectors 203 are arranged below the sample holder plane 211. Each set of position sensitive detectors comprises a first double-layer 220 of drift tubes 204 arranged in the X direction and a second double-layer 221 of 30 drift tubes 204 arranged in the Y direction. In each of the layers 220, 221, the drift tubes 204 are arranged in two rows, offset by half a tube diameter from each other. In the system of FIG. 2, the drift tube modules can be 12-foot long aluminum drift tubes which are configured to measure the position and angle of incoming and outgoing charged particle tracks in X and Y coordinate directions. In each of the X and Y directions of each set of detectors 203, the drift tubes are arranged in two rows, offset by half a tube diameter from each other.

The tubes can be arranged in different ways. For example, the layers need not have to be 90 degrees from one another, but can be smaller non-zero angles. Also by way of example, the top layer could be at 0 degrees, middle layer at 45 degrees from the first, and a third layer 90 degrees from the first. This would allow resolution of multiple tracks that occur at the same instance of time.

Also, other position sensitive detector arrangements capable of scattering the charged particle passing through and providing a total of at least three individual positional measurements can be adopted instead of the arrangement of detectors of FIG. 2. At least 3 position measurements are required so as to enable a line fit with a free parameter from which one can calculate momentum.

Data acquisition electronics 212 can record the hit time and channel number of the drift tubes, where a channel corresponds to each drift tube in the system. One example of the data acquisition electronics 212, operably coupled to the drift tubes, will now be described. Drift tubes of the detector system 200 of FIG. 2 are connected to respective electronic amplifiers (not shown), which increase the voltage of the deposited signal (associated with, e.g., a cosmic ray-produced muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number of the digital signal is registered to the nearest time granularity (e.g., nearest nanosecond) by a time-to-digital-converter (TDC).

Figure 3:
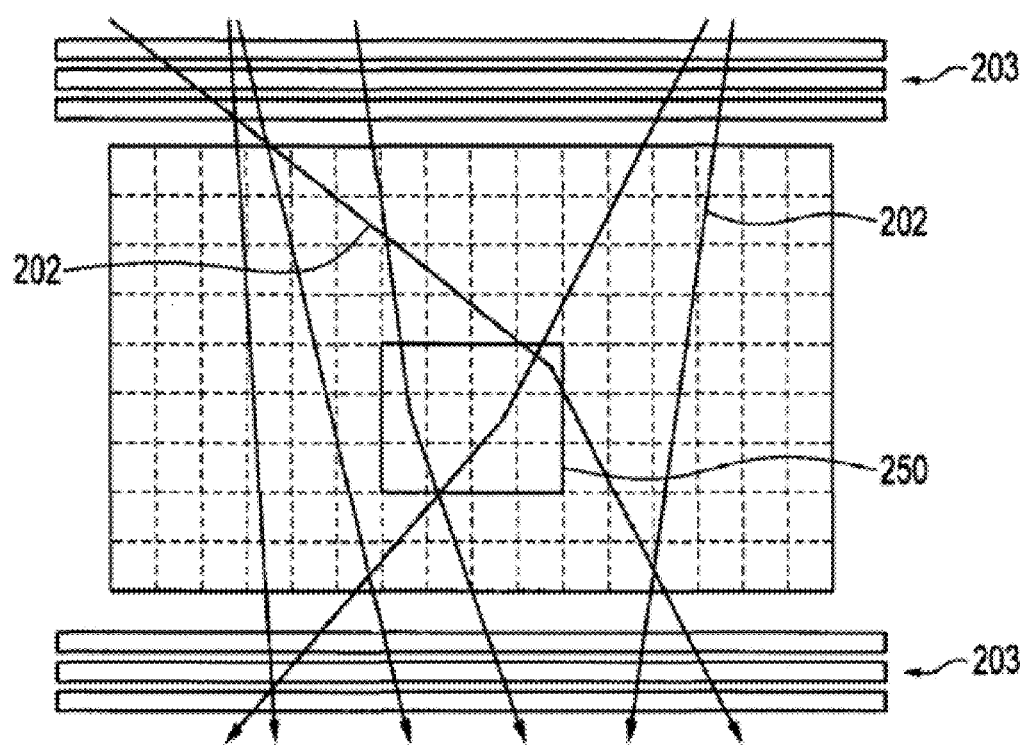
FIG. 3 illustrates a side view of position sensitive detectors arranged above and below a volume occupied by an object under interrogation.

Each drift tube can have its own front-end electronics and TDC. The front-end electronics may be constructed using hardware components such as off-the-shelf (OTS) parts. For example, the TDC can be OTS parts, such as those built by Caen corporation in Italy. Each TDC unit (CAEN 767B) has the capability of 128 input channels (drift tubes in our case), and stores the time of the hit digitally. These units have a buffer that can hold about 32,000 hits. The TDCs are read-out about 5 times per second with a custom data-acquisition system (DAQ). The TDCs sit in a Versa Module Eurocard VME crate with a SIS 1100 controller, made by Struck Innovative Systeme GmbH (SIS), which provides the computer interface. The DAQ can run on a signal processing unit, such as on a personal computer, with an optical cable to interface with the SIS 1100 to command the TDCs for the data transfer. Once the hit times and channel numbers are read out into the memory of the PC, the raw data can be stored on a memory device, such as a hard drive. The data is also processed to identify the cosmic ray (or charged particle) events. The track data and pertinent diagnostic data can also be stored on the hard drive One example of charged particle detector 200 is depicted in FIG. 3, which illustrates a side view of position sensitive detectors 203 arranged above and below a volume occupied by an object 250 under interrogation. The position sensitive detectors 203 detect the incoming and outgoing charged particles that form tracks 202. On each side of the volume to be scanned, the drift tubes can be arranged to enable them to make at least three positional measurements in a first direction and in a second direction (which is different from the first direction) which may be orthogonal or non-orthogonal to the first direction. In some implementations, additional drift tube detectors can be implemented on sides of the volume to form a box or four sided structure into which a package, a vehicle or cargo container can enter for scanning by the system.

Figure 4:
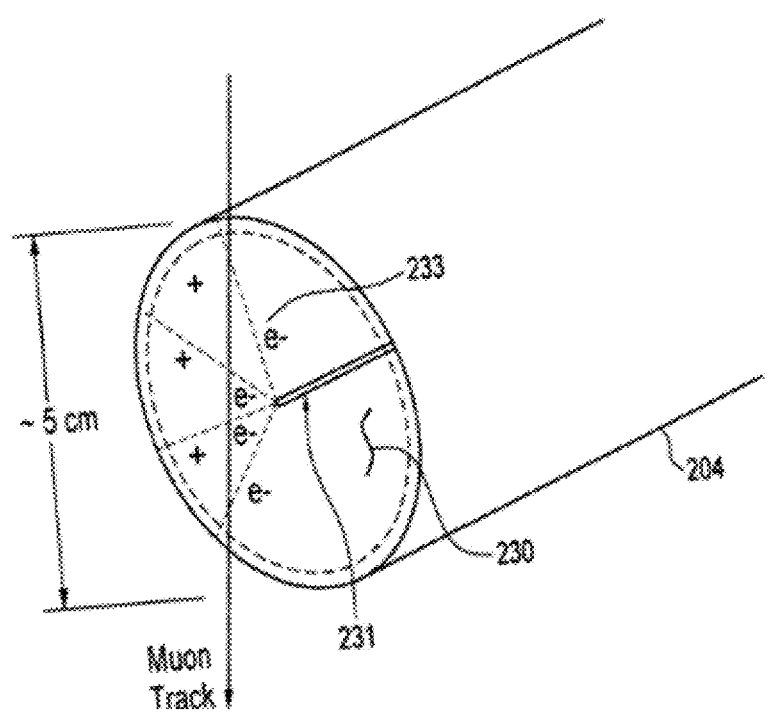
FIG. 4 is a cross-sectional view of part of an exemplary drift tube.

A cross-sectional view of part of a typical drift tube 204 detecting a muon or other charged particle passing through the tube is illustrated in FIG. 4. The drift tube module is typically cylindrical and filled with a detector gas such as Argon-Isobutane 230 to enable detection of the charged particles, such as muons. In one exemplary implementation, the system is configured to apply a positive HV of about +2-3 kV to a central anode wire 231 extending along the length of the cylindrical tube with the tube at ground so that a high-voltage static field is present. When the charged particle interacts with gas atoms, many electrons 233 are liberated from those atoms in a straight line through a chord of the tube. The static field causes the "string" of electrons to drift toward the positively charged anode wire. The anode wire is typically very thin, 0.001" in diameter, creating a very high field near the wire to produce an electron avalanche when the first electron arrives. The avalanche of charge is about 105 electrons per incoming electron, which is easily detected with sensitive electronics.

The anode wire can be read-out electronically with the TDCs of the data acquisition electronics 212. This is how a hit signal is produced when a charged particle moves through the detector drift tube. Although, in one example, the drift tube of FIG. 4 is manufactured from aluminum, other materials such as carbon composite with internal conductive coatings can be adopted instead of aluminum. Further, the drift tubes need not have circular cross-sections. For example, the drift tubes may be constructed from aluminum extrusions with multiple, non-circular cross-sections. Alternatively, drift cells other than drift tubes can be adopted such as for example triangular shaped drift cells. Drift cells having many anode wires, such as small gas drift chambers (GDC), can be used instead of using drift cells having a single anode wire.

The processing of measured data corresponding to the charged particles interactions with the volume under inspection (e.g., a package, a container or a vehicle) allows reconstruction of the trajectory of a charged particle through the volume, measurement the momentum of an incoming muon based on signals from the detectors on each side of the volume, and determining the spatial distribution of the scattering density of the volume. These and other processing results can be used to construct the tomographic profile and measure various properties of the volume such as detecting a target object. The knowledge of the particle's momentum can improve the material density estimate obtained from reconstruction.

Some tomography methods estimate particle momentum for passive tomography systems by relying on additional scattering material and additional detector layers. Other systems estimate the charged particle momentum without the use of additional metal layers, but do so by relating the goodness-of-fit of the particle trajectory to the particle momentum. Unlike such systems, the techniques that are described in this document improve the estimation of the charged particle momentum without requiring the use of additional detector layers or the use of goodness of fit, but rather use the charged particle scattering in materials existing in the detectors. In doing so, the disclosed techniques provide an actual estimation of the amount of scattering within the detectors and utilize a specific relationship between the width of the scattering distribution and the momentum of the charged particle to more accurately estimate the momentum of the charged particles.

As noted above, the incoming and exiting trajectories of charged particle tracks entering and exiting the tomographic volume are estimated using position detectors. The effective scattering angle can thus be calculated from the deviation of the trajectories. The relationship between width of particle's scattering angle distribution $\sigma_\theta$ and momentum p can be characterized as:

$$\sigma_\theta = \frac{13.6 \text{ MeV}}{\beta c p} z \sqrt{L/X_0} \, [1 + 0.038 \, \ln(L/X_0)]. \quad \text{(Eq. 1)}$$

In Equation (1), c is the velocity of light, $\beta$ is a multiplication factor, z is the charge of the particle, L is the thickness and $X_0$ is the radiation length of the scattering material. For muons and electrons that are most relevant for the charged particle tomography application, the charge, z, is one, and the particle energy is high enough such that it can be assumed that the particle is traveling at the speed of light, or with $\beta$ of one. Equation (1) can then be simplified as:

$$\sigma_\theta = \frac{13.6 \text{ MeV}}{c p} \sqrt{L/X_0} \, [1 + 0.038 \, \ln(L/X_0)]. \quad \text{(Eq. 2)}$$

In one particular configuration, the position detector includes multiple orthogonal layers of drift tubes, with each drift tube situated in a layer such that it provides a localized position of where the particle intersects the drift tube. The charged particle's points of scattering in the position detector can be calculated per layer. In one configuration, where each layer includes two rows of drift tubes, the point of scattering for a given layer is the centroid of all the measured positions on that layer.

To obtain a measurement of the particle scattering in the detector, an estimate of the particle's trajectory at the point of scattering is needed. This local trajectory is different from the particle's incoming and exiting trajectories, which are linear fits of the position measurements, in that multiple local trajectories combine to form a non-linear particle path through the layers of drift tubes. Each local trajectory is defined as a vector connecting one point of scattering to the next point of scattering that does not cross the tomographic volume.

In the above described system, each drift tube layer has a coordinate direction (along the length of the drift tube) with a position resolution that is worse relative to the other two directions. Thus, to mitigate the potential for obtaining a larger scattering estimate due to inferior resolution in one position coordinate, the local trajectory connects two scattering points on parallel layers (i.e. layers with drift tubes oriented in the same direction).

An additional motivation for connecting scattering points on parallel layers is due to the limitation imposed by the timing resolution of the system. Because the orthogonal drift tube layers are placed in alternating order, there is a greater separation between parallel layers than there is between consecutive layers, which provides a greater sensitivity in measuring the displacement perpendicular to the particle trajectory and the proportional scattering angle.

Figure 5:
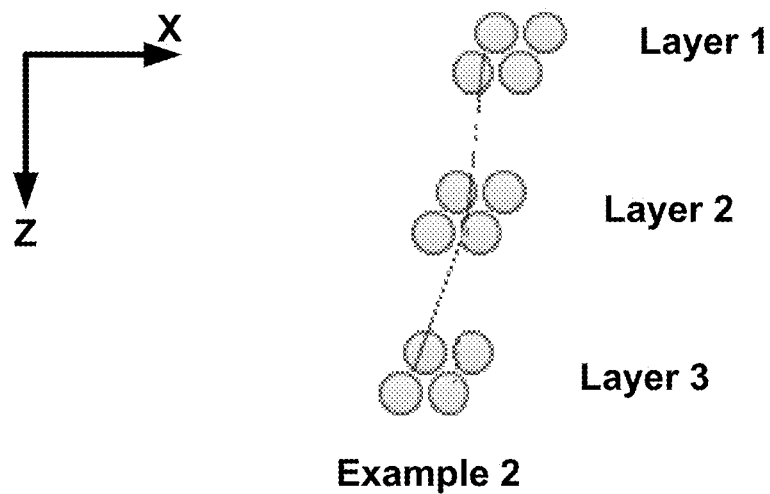
FIG. 5 illustrates two examples of local trajectories among three layers of drift tubes of similar orientation.
Figure 5:
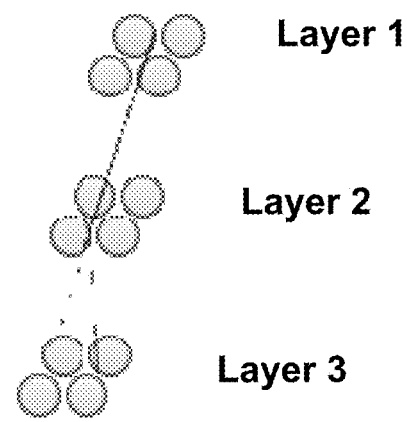

FIG. 5 illustrates two examples of local trajectories among three layers of drift tubes of similar orientation. The deviations due to scattering are illustrated (in an exaggerated manner) by the angle between the local trajectory (solid line) and the projected un-scattered trajectory (dotted line) of the previous local trajectory.

Measuring Deviations Of Local Trajectories: The distribution of scattering angles, the width of which is inversely proportional to momentum, includes angles that measure the deviation of local trajectories relative to a reference trajectory. In one example, the reference trajectory is the average of all local trajectories. The charged particle trajectory can have an arbitrary angle in a 3-dimensional coordinate space. In a Cartesian coordinate system, the particle trajectory can be projected in, for example, the x-z and y-z orthogonal planes. The deviation due to scattering in each of the two orthogonal directions (e.g., x-direction in the x-z plane and y-direction in the y-z plane) are independent of each other and proportional to the 3-dimensional scattering angle, $\sigma_\theta^{3D}$. The distribution of the deviation in each orthogonal direction, $\sigma_\theta^{plane}$, is given by:

$$\sigma_\theta^{plane} = \frac{1}{\sqrt{2}} \sigma_\theta^{3D}. \quad \text{(Eq. 3)}$$

To maximize the number of samples in the scattering angle distribution, the deviation of each local trajectory is measured in each orthogonal direction separately. For example, scattering angles in x- and y-directions are calculated by projecting the two trajectories onto the x-z and y-z planes, respectively. As noted earlier, the position detector's resolution is better in the direction perpendicular to the drift tube length, which allows smaller angle measurements to be measured in the perpendicular direction. It should be noted that the disclosed techniques are not exclusive to the Cartesian coordinate system and can be used in other coordinate systems (e.g., the spherical coordinate system), as well. FIG. 6(a) is an exemplary plot that illustrates the distribution of charged particle scattering angles (on a logarithmic scale) inside the position detectors. As evident in FIG. 6(a), the distribution in a perpendicular direction of the tube length (labeled as "Across") is shifted to the left compared to the distribution of the scattering angles in direction along the tube length.

Figure 6B:
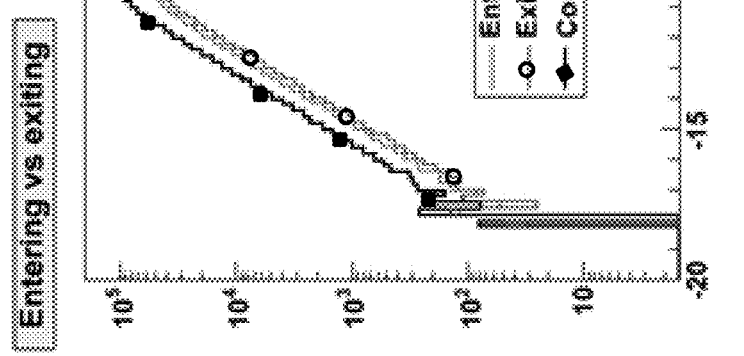
FIG. 6(b) is an exemplary plot that illustrates the distribution of charged particle scattering angles for the incoming and exiting charged particle sets of detectors.
Figure 6A:
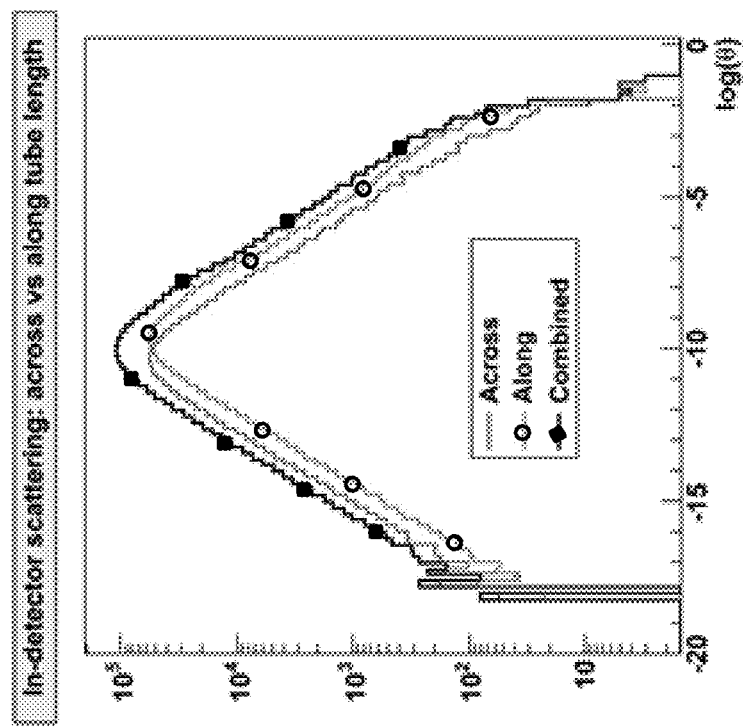
FIG. 6(a) is an exemplary plot that illustrates the distribution of charged particle scattering angles inside the position detectors.

FIG. 6(b) is an exemplary plot that illustrates the distribution of charged particle scattering angles (on a logarithmic scale) for the incoming and exiting charged particle sets of detectors. The particle's scattering angle distributions as it enters and exits the sets of detectors, on average, are similar to in-detector scattering angle distributions. FIG. 6(b) also shows that the exiting beams exhibit slightly larger angles compared to the entering beams, which may be due to the exiting particle having a smaller momentum due to energy loss.

Width Of In-Detector Scattering Angles: The width of the scattering angle distribution for local trajectories may be obtained as the root mean square (RMS) of all (e.g., n) the scattering angles for a given charged particle, as provided by Equation (4):

$$Scattering\,Width = \sqrt{\frac{\sum_n \theta}{n}}. \quad \text{(Eq. 4)}$$

Figure 7B:
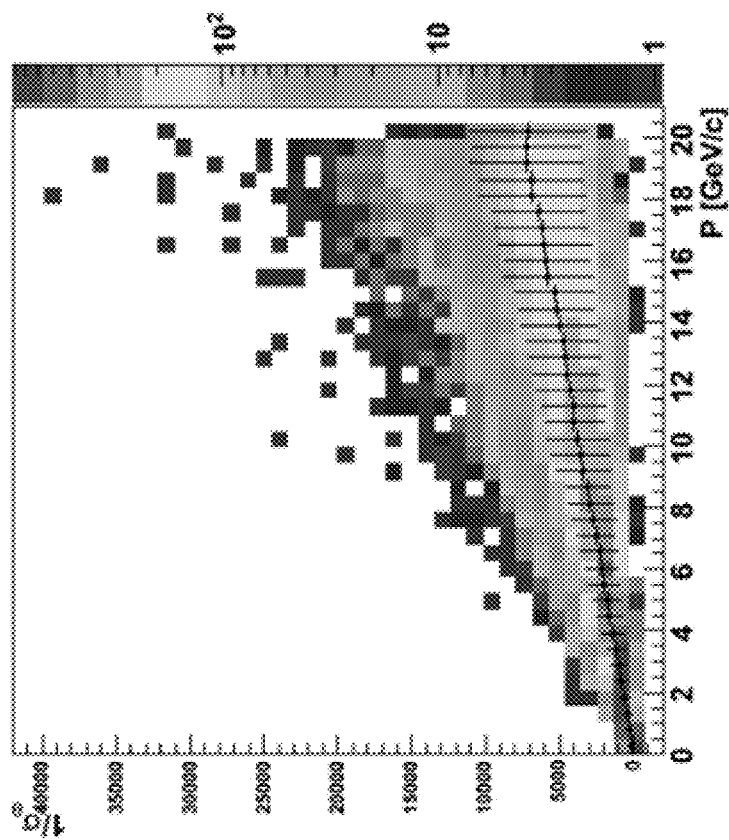
FIG. 7(b) is an exemplary plots that shows the relationship between the inverse scattering width versus the muon momentum.
Figure 7A:
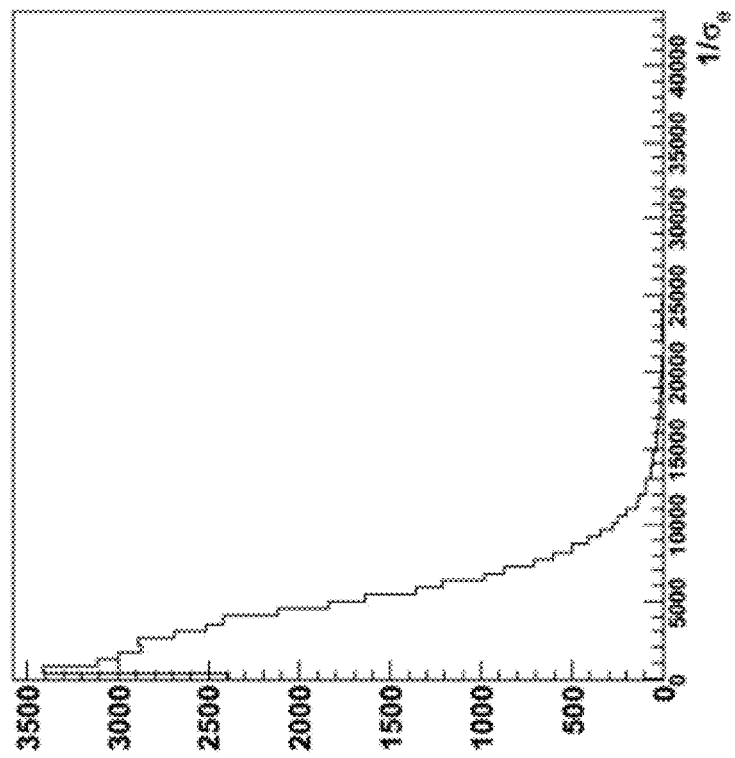
FIG. 7(a) is an exemplary plot of the distribution of the inverse of the width of the distribution of the scattering angles inside the position detectors.

FIG. 7(a) is an exemplary plot of the distribution of the inverse of the width of the distribution of the scattering angles inside the position detectors for simulated muons. FIG. 7(b) is an exemplary plot that shows the linear relationship between the inverse scattering width (shown on the vertical axis) versus the muon momentum.

Length Of Scattering Material: The next element that is needed to obtain the momentum is the thickness, L, of the scattering material. The scattering material is the material traversed by the charged particle. Some materials (e.g., aluminum) cause more scattering than others (e.g., air). The radiation length can be computed using the composite sum of all the different radiation lengths of all the different traversed material. In practice, however, some materials that contribute little to the scattering can be neglected. The length of scattering, thus, can represent the length of material that is not neglected. For example, if only drift tube walls are assumed to contribute to the scattering, L is the charged particle pathlength through the drift tube walls. In crossing the position detectors, the charged particle traverses through the layers of drift tubes, which includes both the walls of the drift tubes and drift gas inside of the drift tube. For simplicity, in some implementations, the contribution of the drift gas to the overall scattering thickness is ignored since the gas radiation length is significantly greater than the radiation length of the drift tube wall. The contributions of the drift gas, however, can be readily included in other implementations, where it may be significant enough to affect the momentum estimate. In one exemplary implementation of the system, the drift tube wall made of aluminum, with a radiation length of 8.897 cm.

FIG. 8(a) is a simplified diagram of the charged particle's pathlength through a drift tube in the plane perpendicular to the direction of the tube length orientation. In FIG. 8(a), t represents the thickness of the walls of the drift tube, $R_{inner}$ represents the radius of the drift tube, and $r_{drift}$ represents the drift radius, which is the closest distance between the charged particle's trajectory through the drift tube and the drift tube anode wire. FIG. 8(b) is another simplified diagram that shows the charged particle's pathlength through a drift tube in the plane parallel to the direction of drift tube length orientation, with $\alpha_{\|,incoming}$ representing the particle's incident angle projected along the direction of tube length.

The particle's pathlength in the drift tube wall, as illustrated in, for example, FIGS. 8(a) and 8(b), can be twice the wall thickness, t, corrected for the drift radius, $r_{drift}$ and the particle's incident angle projected along the direction of tube length, $\alpha_{\|,incoming}$. The overall thickness of scattering material, L, for i number of tubes, is then given by:

$$L = \sum_i^{tubes} \left( \frac{2 \cdot \left( \sqrt{(R_{inner} - t)^2 - (r_{drift}^i)^2} - \sqrt{R_{inner}^2 - (r_{drift}^i)^2} \right)}{\cos(\alpha_{\|,incoming})} \right). \quad \text{(Eq. 5)}$$

It should be noted that in Equation (5), only the drift tube walls are considered as scattering material. The particle's incoming angle in the plane perpendicular to the drift tube length is not expected to affect its pathlength because of the symmetry of the cylindrical drift tube. However, the particle's incoming angle in the plane parallel to the drift tube length does affect its pathlength, as the drift tube effective thickness is greater for particles that are more parallel with the drift tube.

Figure 9:
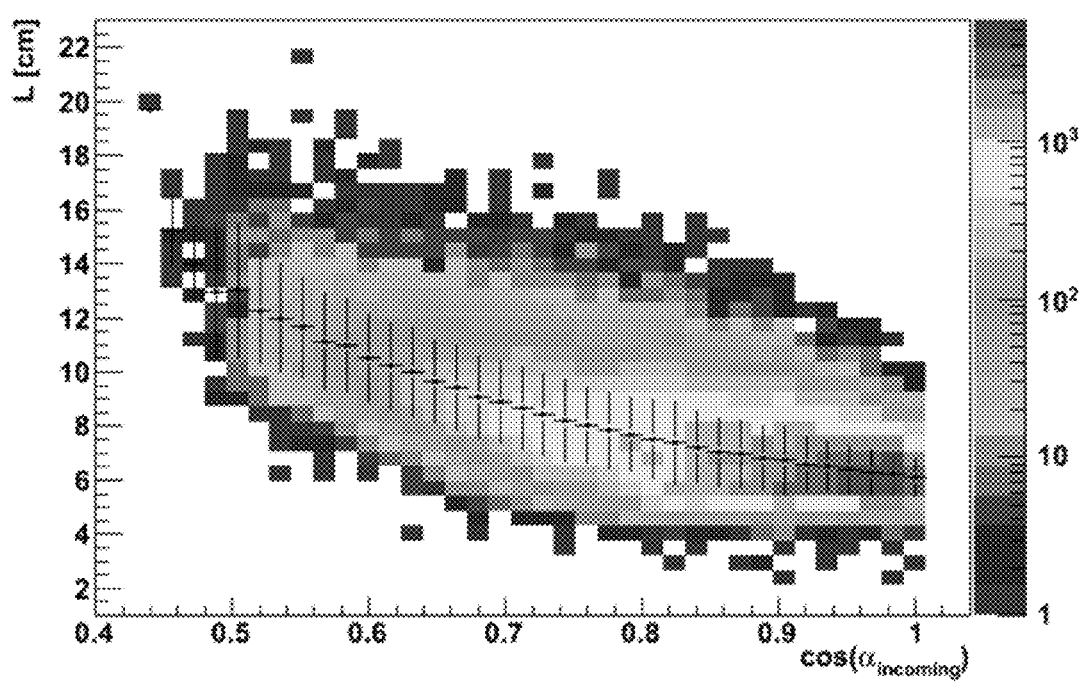
FIG. 9 illustrates an exemplary estimated scattering pathlength for a particle in a position detector on a logarithmic scale as a function of the cosine of the particle's incoming angle with respect to the zenith.

FIG. 9 illustrates an exemplary estimated scattering pathlength for a particle in a position detector on a logarithmic scale (see vertical scale on the right side) as a function of the cosine of the particle's incoming angle with respect to the zenith, $\alpha_{incoming}$. The average pathlength per $\cos(\alpha_{incoming})$ is shown by the solid line and is observed to be increasing for particles with greater zenith angle.

Once the width of the scattering angle, $\sigma_\theta$, and scattering pathlength, L, are estimated, based on Equations (2) and (3), the momentum, p, can be obtained using the following relation:

$$p = f \cdot \frac{13.6 \text{ MeV}}{\sqrt{2} \, \sigma_\theta^{plane} c} \sqrt{L/X_0} \, [1 + 0.038 \, \ln(L/X_0)]. \quad \text{(Eq. 6)}$$

In Equation (6), f is an empirical proportional factor that is determined from simulation data and verified using experimental data.

Figure 10:
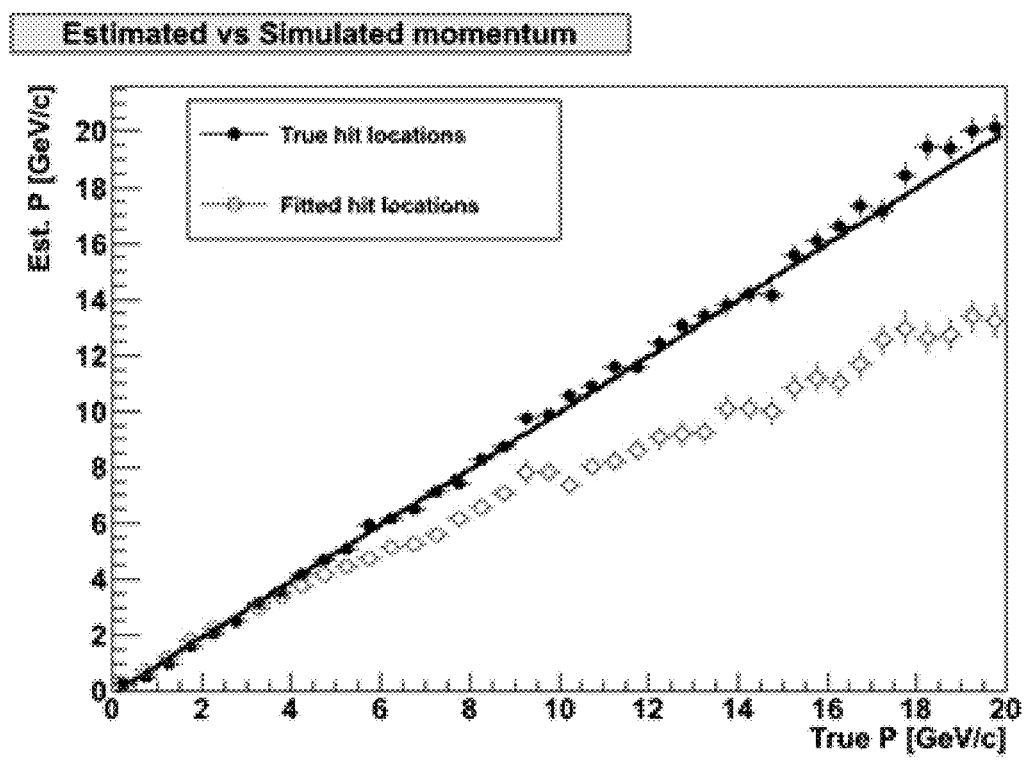
FIG. 10 is a plot of estimated momentum based on the disclosed techniques versus the true momentum.

The disclosed techniques have been verified using a working prototype implementation. Applying the disclosed techniques to the simulated muons with known positions generate estimated momentum values that are strongly correlated to the true momentum values. In practice, the true positions of where the particle crosses the drift tubes are not known but estimates obtained from applying a track fitting algorithm to timing information are available. The error in these estimates may thus impact the accuracy of the results obtained through the application of the disclosed techniques for certain momentum regions (e.g., at a higher momentum region). FIG. 10 is a plot of estimated momentum based on the disclosed techniques versus the true momentum. The plot illustrates, as filled circles fitted with a solid line, the estimated momentum as calculated by the method for simulated muons, as well as the momentum values based on the estimated positions using a track fitting algorithm (open circles without a fitted line).

The disclosed techniques and systems and implementations improve the accuracy and resolution of the momentum estimate for both scattering and stopping particles used in tomographic reconstruction. A stopping particle is a charged particle that is detected by the "in" position detector (e.g., the first set of detectors), but not detected by the "out" position detector (e.g., the second set of detectors). It is likely that the stopping particle is a lower energy electron or muon that is absorbed by the material in its path, instead of merely being scattered. Such improved momentum estimations can lead to improved image quality by, for example, improving the measured contrast between different density materials. Improved image quality from scattering particles can consequently lead to improved probability of detection of distributed special nuclear material (SNM) and other high-density contraband, while improved image quality from stopping particles can consequently lead to improved detection of other low-to medium-density contraband.

Figure 11:
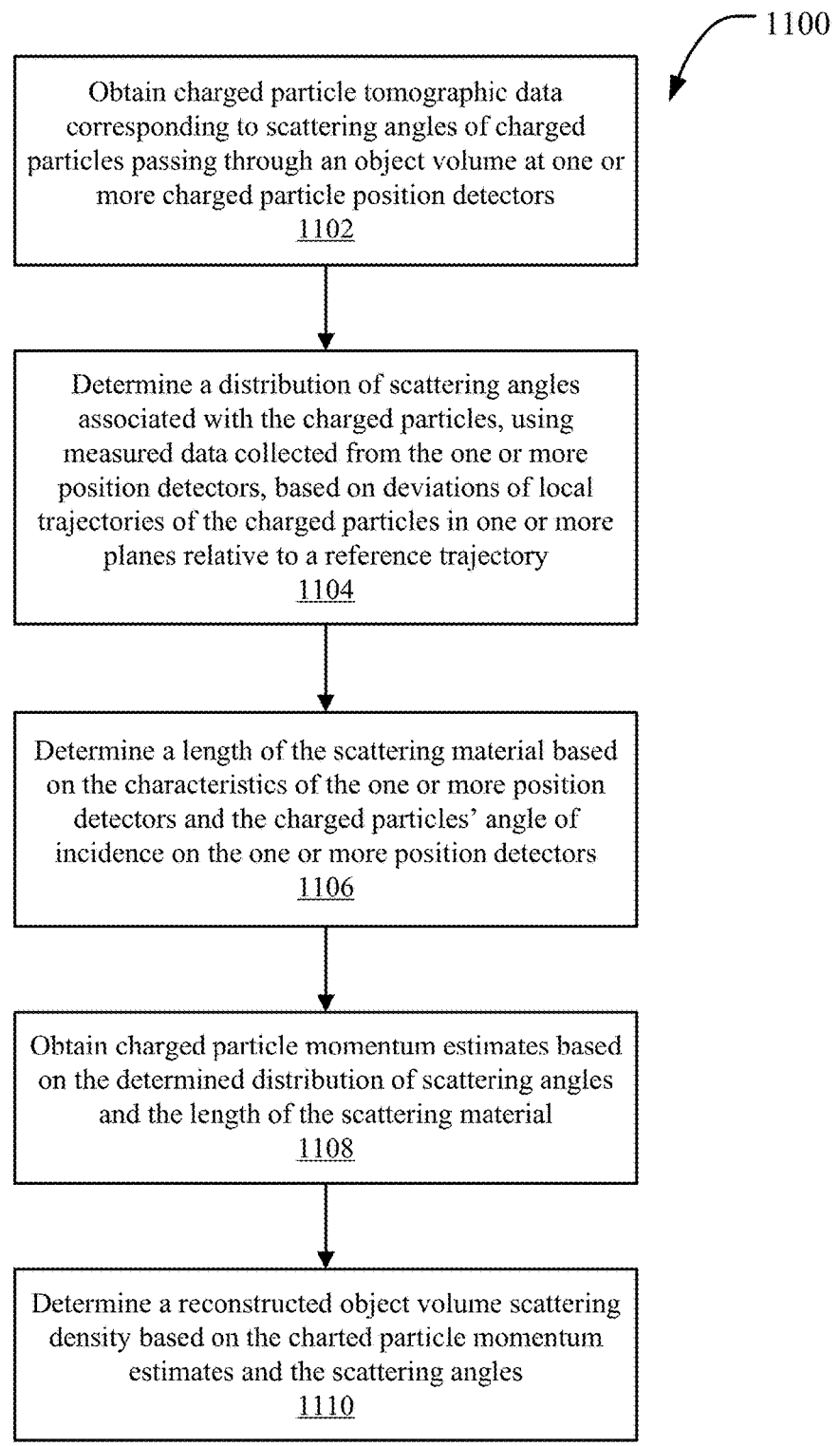
FIG. 11 illustrates a set of operations that can be carried out to obtain charged particle momentum estimates and to detect an object volume from charged particle tomographic data in accordance with an exemplary embodiment.

FIG. 11 illustrates a set of operations 1100 that can be carried out to detect an object volume from charged particle tomographic data in accordance with an exemplary embodiment. At 1102, charged particle tomographic data is obtained that corresponds to scattering angles of charged particles passing through an object volume at one or more charged particle position detectors. At 1104, a distribution of scattering angles associated with the charged particles is obtained, using measured data collected from the one or more position detectors, based on deviations of local trajectories of the charged particles in one or more planes relative to a reference trajectory. At 1106, a length of the scattering material is determined based on the characteristics of the one or more position detectors and the charged particles' angles of incidence on the one or more position detectors. At 1108, charged particle momentum estimates are obtained based on the determined distribution of scattering angles and the length of the scattering material. At 1110, a reconstructed object volume scattering density is obtained based on the charged particle momentum estimates and scattering angles. For example, the scattering angles indicate the change in trajectories between the first and the second set of detectors.

Reconstruction of the object volume scattering density can be done using various methods. In one example, such reconstruction can be done using a maximum likelihood estimate of the object volume scattering density based on an expectation maximization (ML/EM) algorithm. Such an algorithm is described in the PCT Application with Publication No. WO2008/140559, which is incorporated herein by reference.

Various embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

In another aspect, the disclosed technology can be used to implement momentum estimation of cosmic ray muons through multiple scattering in muon tomography scanner. In a muon tomography (MT) detector system, the multiple Coulomb scattering of cosmic ray muons is used to infer the scattering density of materials placed within the detector inspection volume. Because the Coulomb scattering depends on the property of the materials as well as the particle momentum, image reconstruction algorithms for MT utilize the muon momentum to improve the resulting image and improve discrimination between lower and higher scattering density materials. The disclosed technology provides for a method to estimate muon momentum using its scattering within the detector itself. Results on simulated muon tracks and application to observed muon tracks are also provided.

The Multi-Mode Passive Detection System (MMPDS) is a muon tomography (MT) scanner that includes at least two sets of detectors (SuperModules) placed approximately 5 m apart above and below an inspection volume. Each set of detectors includes multiple orthogonal layers of parallel drift tubes. The top detector measures the incoming trajectory of a passing muon, while the bottom detector measures its outgoing deflected trajectory. A charged particle incident on a seal drift tube ionizes the drift tube gas, generating an electric signal that is read out separately for each drift tube. Coincidence of drift tube hits within a time window creates a track event. Set of drift tubes hits within an event is used to estimate particle trajectory, with timing information used to estimate drift radius. Particle trajectory, scattering angle, and momentum are used to reconstruct 3D representation of the materials inside the inspection volume. The change in direction and momentum of muons that pass through the detectors and the materials within the inspection volume can give insight into the properties of the materials.

The width of the Coulomb scattering of a particle through a material depends on the particle's momentum. Over the same material, on average, higher energy particles scatter less than their lower energy counterparts. In MT, this results in an underestimation of the scattering signal from high-energy muons, and an overestimation of the scattering signal from low energy muons. A good muon momentum estimate would counteract this effect and potentially improve the contrast between materials of different scattering density in reconstructed images.

Each drift tube is read out as a separate channel. The multiple layers of drift tubes in the MT detector provide multiple measurements of an incident muon. These measurements (hits) are inputs into a track-fitting algorithm that reconstructs an estimated linear muon trajectory. The multiple scattering of the muon due to the drift tubes introduces deviations from its trajectory, and assuming a Gaussian angular distribution, the width of the scattering angles from these deviations, $\sigma_\theta$, is given by equation (7).

$$\sigma_\theta = \frac{13.6 \text{ MeV}}{\beta c p} \sqrt{x/X_0} \left[1 + 0.038 \ln(x/X_0)\right] \quad \text{Eq. (7)}$$

where $\beta c$ is the velocity and p is the momentum of the muon, x is the thickness and $X\_0$ is the radiation length of the scattering material.

A set of scattering angles representing the deviations in muon trajectory is obtained from the relative positions of the drift tube hits. An estimate of the muon momentum is then calculated using equation (7) from the measured width of these angles and estimated scattering material thickness in radiation length ($x/X_0$) based on the muon path length through the drift tube hits observed, assuming a relativistic muon traveling at the speed of light.

For each muon, its incoming momentum, before it enters the inspection volume, is estimated using the width of scattering angles measured, and estimated path length in materials in the top detector. Similarly, its outgoing momentum, after it exits the inspection volume, is estimated from the measured scattering angles and estimated path length in the bottom detector. An average momentum is estimated using the width of the combined distribution of all scattering angles measured in the detectors.

Simulated Muons: To evaluate the effectiveness of the method, 2.4 million simulated muons with known momentum were generated using GEANT4 and stepped through a simulation of an empty half-length MMPDS. The muon momentum is estimated using the above method using the exact positions of simulated drift tube hits and also with drift tube hits' positions estimated by the track-fitting algorithm. The estimated momenta are then compared to the muon's true momentum.

Figure 12:
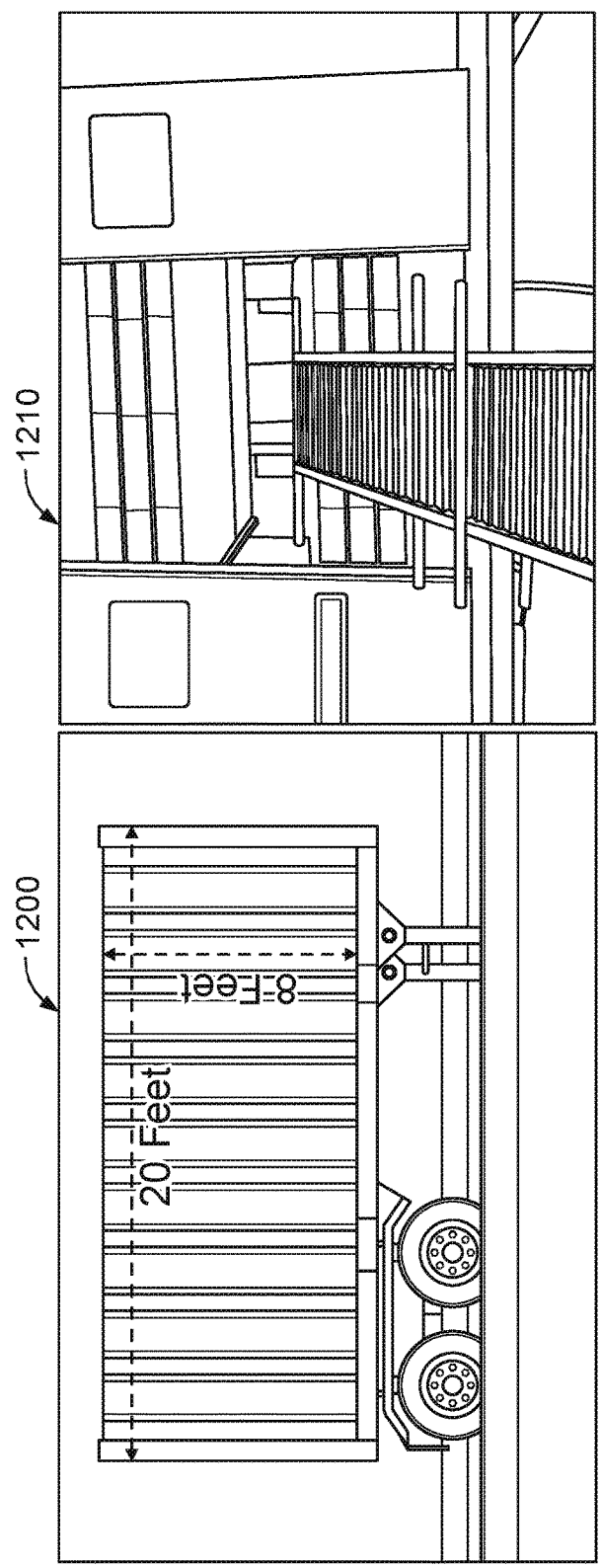
FIG. 12 shows a half-length MMPDS and a package-sized MT scanner that are operational.

Additional simulated muons were also generated for the Package Scanner Demonstration Vehicle (PSDV), a package-sized MT scanner installed in a box truck and measuring approximately 6' by 8' with 33" separation (FIG. 12), with each one of three different objects as listed in Table 1 located at the center of the inspection volume, and also with an empty volume. For comparison with the data recorded using the PSDV, these simulated muons were generated with a power-law momentum spectrum that approximates the natural spectrum of cosmic ray muons. FIG. 12 shows a half-length MMPDS (1200) and a package-sized MT scanner (1210) that are operational. Each system includes at least two SuperModules placed apart to measure muons' incoming and deflected trajectories.

TABLE I

Materials and sizes of test objects.

| Material | Size |
|---|---|
| Aluminum | 7.5" × 7.5" × 8" |
| Steel | 6" × 4" × 5.375" |
| Lead | 4" × 6.5" × 4.25" |

Figure 13:
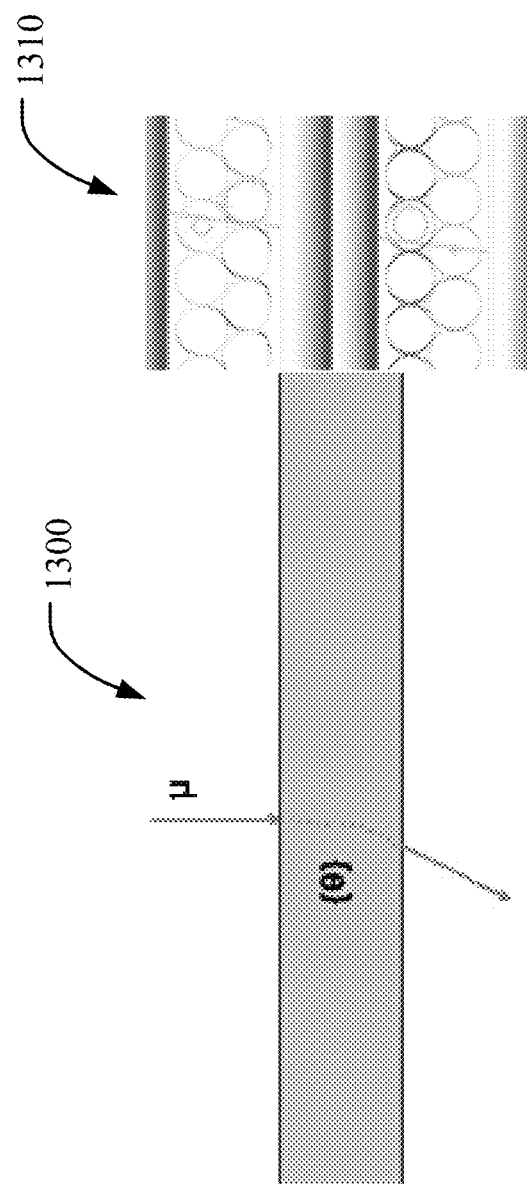
FIG. 13 shows on the left, a muon particle incident upon the MMPDS that undergoes multiple scattering as it traverses through one or more SuperModules.

FIG. 13 shows on the left (1300), a muon particle incident upon the MMPDS that undergoes multiple scattering as it traverses through one or more SuperModules. $\sigma_\theta$ is obtained from a set of measured angular deviations, and the material thickness, $x/X_0$, is calculated based on the shape, size, and material of individual components of the SuperModules. The scattering illustrated above is greatly exaggerated. The actual measured scattering over a single SuperModule is in the order of a few milliradians. The image on the right illustrates the track-fitting algorithm, which estimates each drift tube hit's radius and position, and the particle's fitted trajectory based on all the hits of the event.

Observed Muons: To evaluate how the calculated momentum is affected by the scattering of muons by different materials, an hour-long data run of each was taken with an empty inspection volume, and each object in Table 1 in the center of the volume. The momentum of muons incident on the system is estimated using this method, and muons which trajectory is projected to have passed through the test objects are analyzed further.

Figure 14:
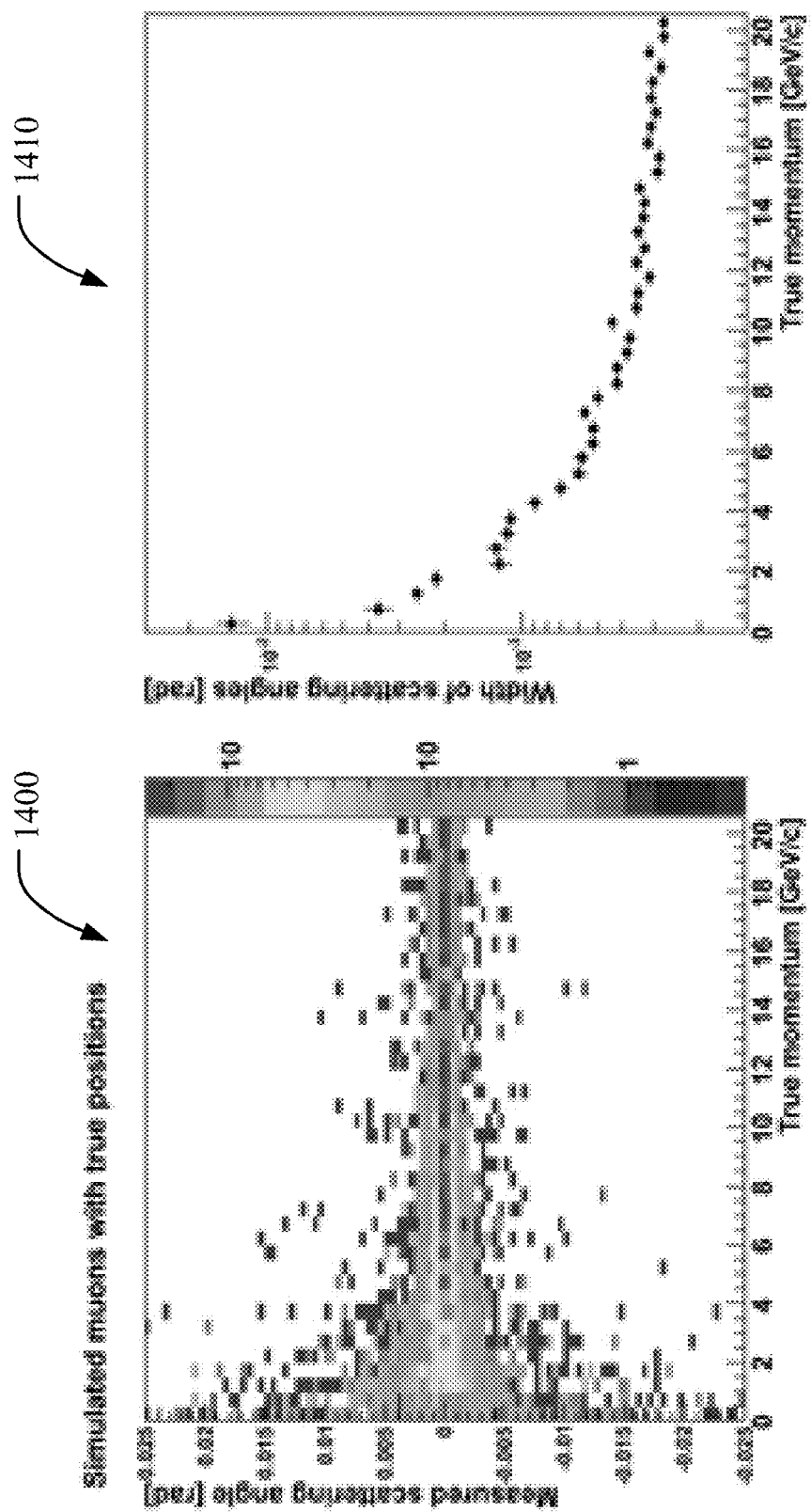
FIG. 14 shows the distribution of muon scattering angles measured in the SuperModules plotted against the known muon momentum.

Results: The width of the distribution of scattering angles from the multiple scattering of a muon in SuperModule(s) is dependent on the muon's momentum. This expected momentum dependence is observed in the distribution of scattering angles inferred from the positions of drift tube hits of simulated muons. As seen in FIG. 14, the width is inversely proportional to the known momentum, which validates these measured scattering angles as reasonable representations of the muon's scattering within the SuperModules. FIG. 14 shows the distribution of muon scattering angles measured in the SuperModules plotted against the known muon momentum (1400). The width of the distribution is shown to be inversely proportional to the muon momentum as expected (1410).

Figure 15:
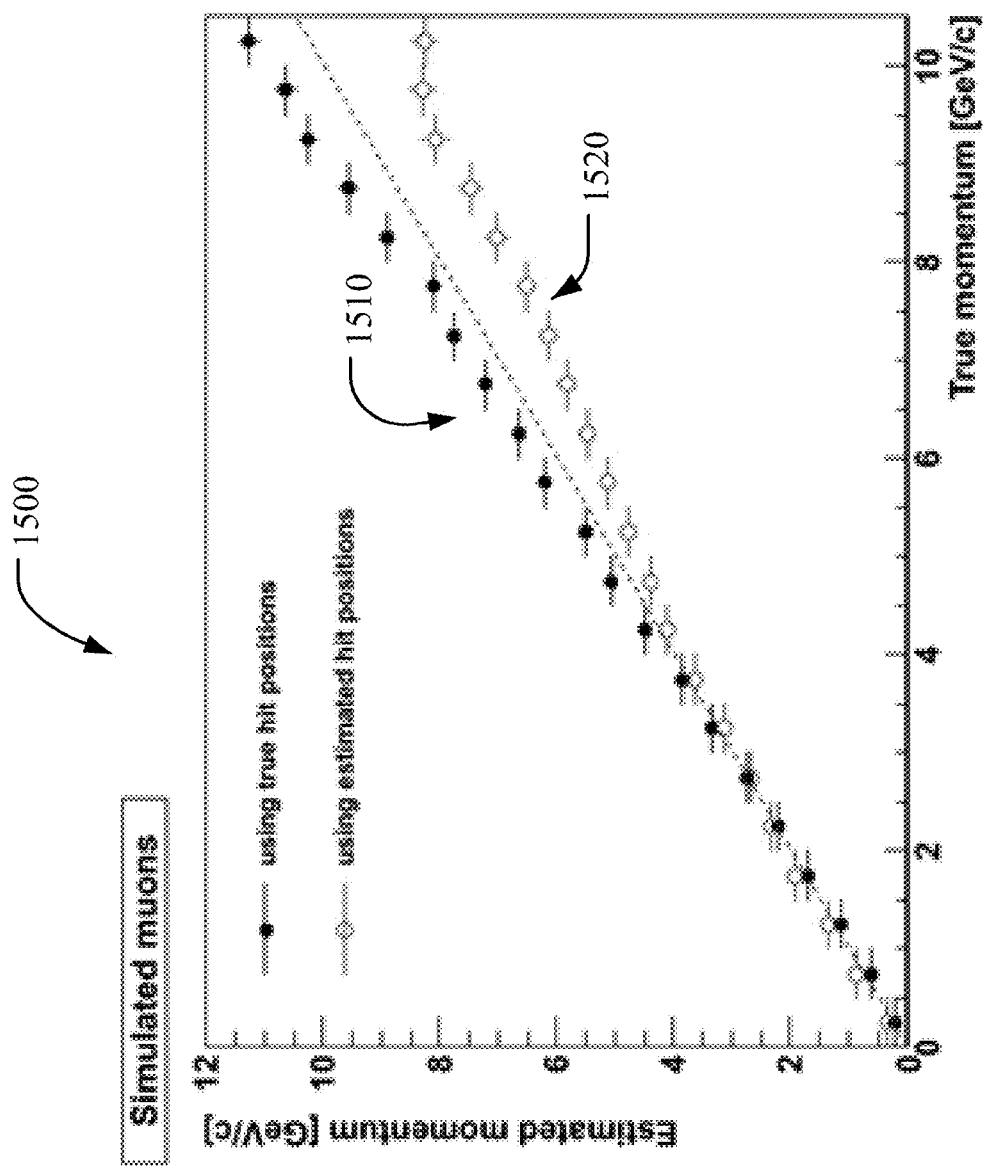
FIG. 15 is a chart that shows that strong correlation is observed between true momentum and estimated momentum when the muon's true hit positions are used (solid, black); however, the correlation weakens at higher momentum when using estimated hit positions resulting from the track-fitting process (open, red).

A plot of the momentum estimate of simulated muons relative to its true momentum (FIG. 15) shows a linear relationship. The introduction of errors into the drift tube measurements weakens the correlation at higher momentum. FIG. 15 is a chart 1500 that shows that strong correlation is observed between true momentum and estimated momentum when the muon's true hit positions are used (solid, black 1510); however, the correlation weakens at higher momentum when using estimated hit positions resulting from the track-fitting process (open, red 1520).

Figure 16:
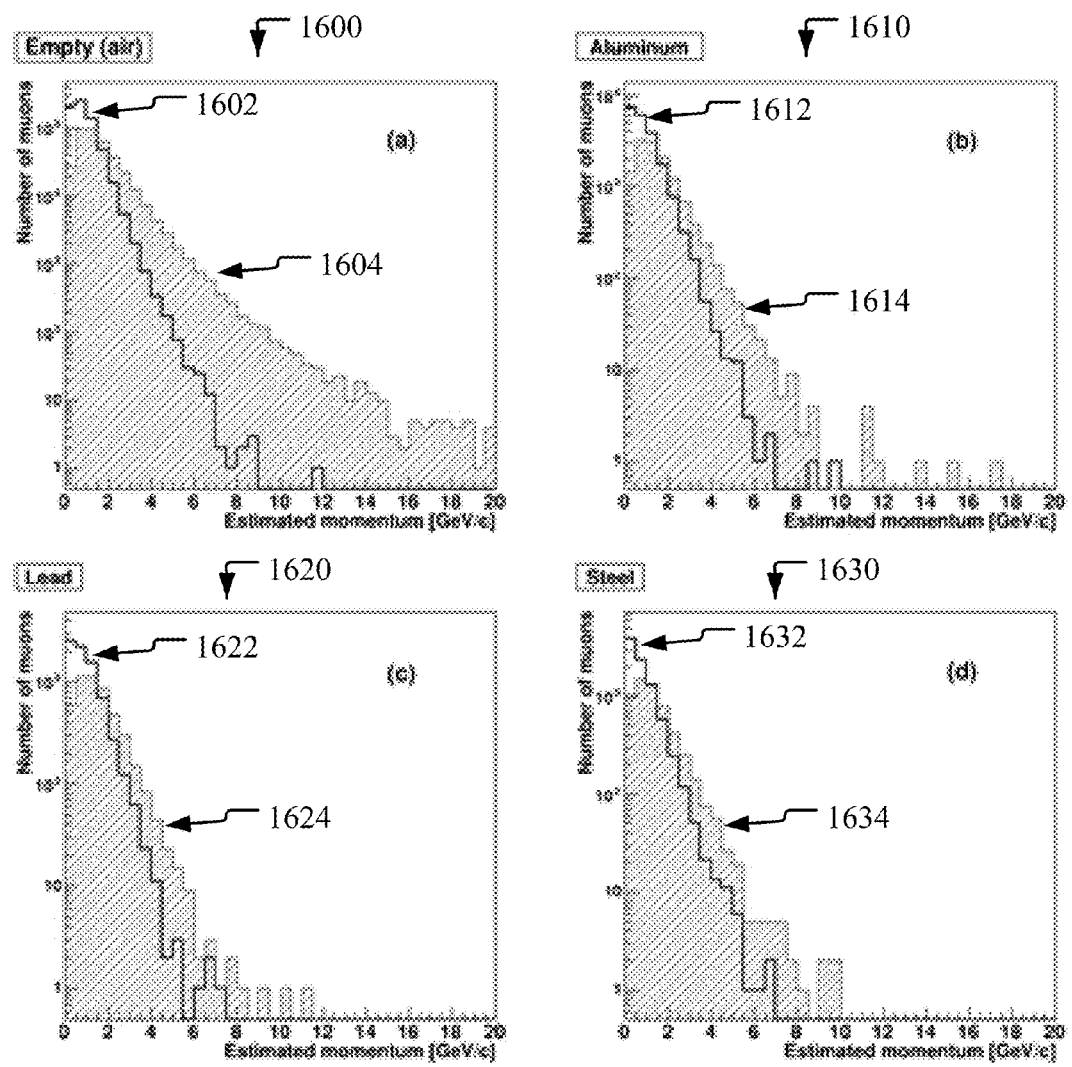
FIG. 16 shows momentum spectra of muons passing through (a) an empty volume, (b) a block of aluminum, (c) a block of lead, and (d) a block of steel for simulated muons with estimated hit positions (blue line) and muons observed by the PSDV (shaded red).

The overall distribution of the estimated momentum of muons measured through the different contents of the PSDV is compared to the corresponding simulated data to evaluate their agreement in FIG. 16. FIG. 16 shows momentum spectra of muons passing through (a) 1600 an empty volume, (b) 1610 a block of aluminum, (c) 1620 a block of lead, and (d) 1630 a block of steel for simulated muons with estimated hit positions (blue line 1602, 1612, 1622, and 1632) and muons observed by the PSDV (shaded red 1604, 1614, 1624, and 1634). Muons are considered to have passed through the object within the PSDV volume if the line of its trajectory intersects the volume occupied by the object. However, this criterion may include muons that did not actually intersect the object, or did not travel through the full thickness of the block. In all cases, the simulated spectrum is harder than the spectrum of observed muons.

Figure 17:
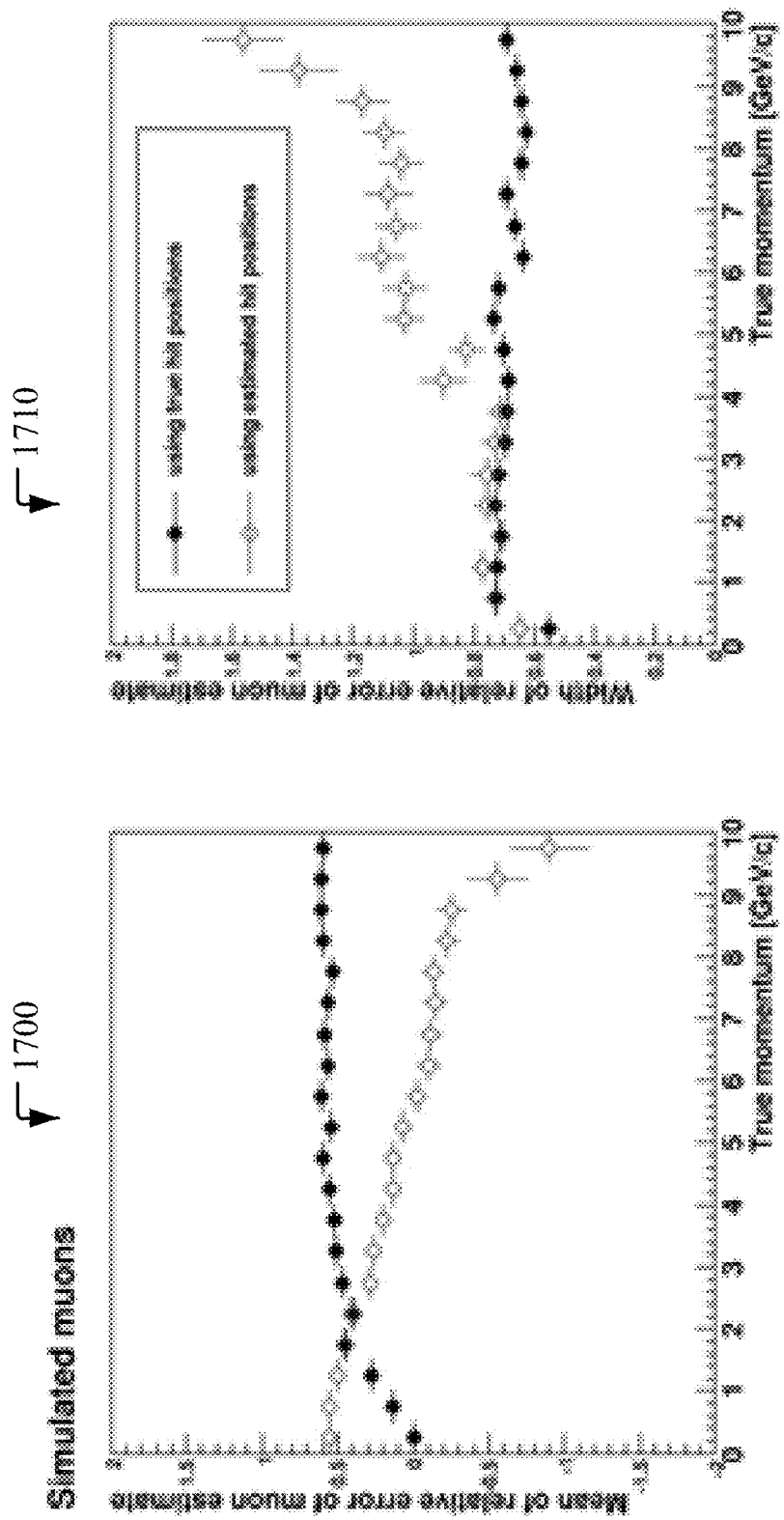
FIG. 17 shows the mean and width of the error on the estimate relative to the true momentum show greater error and uncertainty in the momentum of higher energy muons when estimated hit positions are used.

Our method to estimate momentum shows promise, as evidenced by FIG. 17. Below 3 GeV, which includes more than 90% of expected muon flux, there is a less than 60% momentum-dependent error in the resulting estimate. Based on the relative error shown in FIG. 17, the estimate is better at lower momentum region when true hit positions are used. FIG. 17 shows the mean (1700) and width (1710) of the error on the estimate relative to the true momentum show greater error and uncertainty in the momentum of higher energy muons when estimated hit positions are used.

Figure 18:
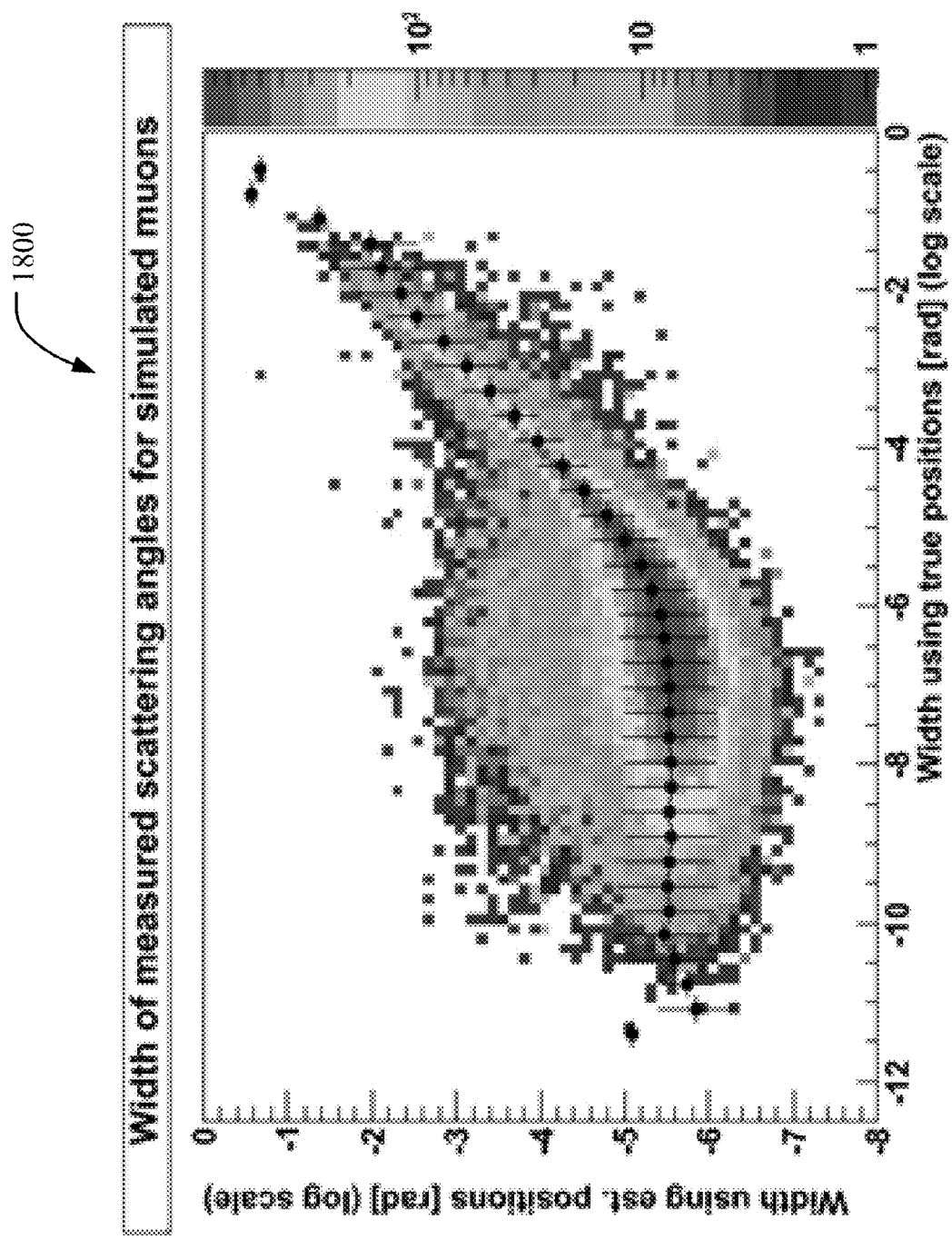
FIG. 18 is a diagram that shows an event-by-event comparison between the measured width of scattering angles when using true and estimated hit positions, showing the limited resolution of estimated hit positions effectively results in lower limit on the width that can be measured.

When estimated hit positions are used, the relative error is larger for both low and high momentum muons. The poorer estimate for high-energy muons is expected because of the limited resolution of hit position estimates. Errors in hit positions result in the larger scattering angles being measured within the detectors, and consequently greater width and lower momentum. An event-by-event comparison between the measured width of scattering angles when using true and estimated hit positions in FIG. 18 shows this limiting effect on the width from estimated positions, which plateaus even as smaller widths from true positions are measurable to lower values. FIG. 18 is a diagram 1800 that shows an event-by-event comparison between the measured width of scattering angles when using true and estimated hit positions, showing the limited resolution of estimated hit positions effectively results in lower limit on the width that can be measured.

The difference in momentum spectra between simulated and observed muons (FIG. 16) can be attributed to the same reason. There are additional errors, such as from the data acquisition electronics, which are not accounted for in the simulation and further reduces the resolution of hit positions and ultimately results in a softer spectrum with more low momentum muons.

A possible explanation for the larger error at low momentum is that the larger deflections of lower energy muons are smoothed and reduced in magnitude as a result of the track-fitting process, resulting in slightly higher momentum estimate than otherwise.

Figure 19:
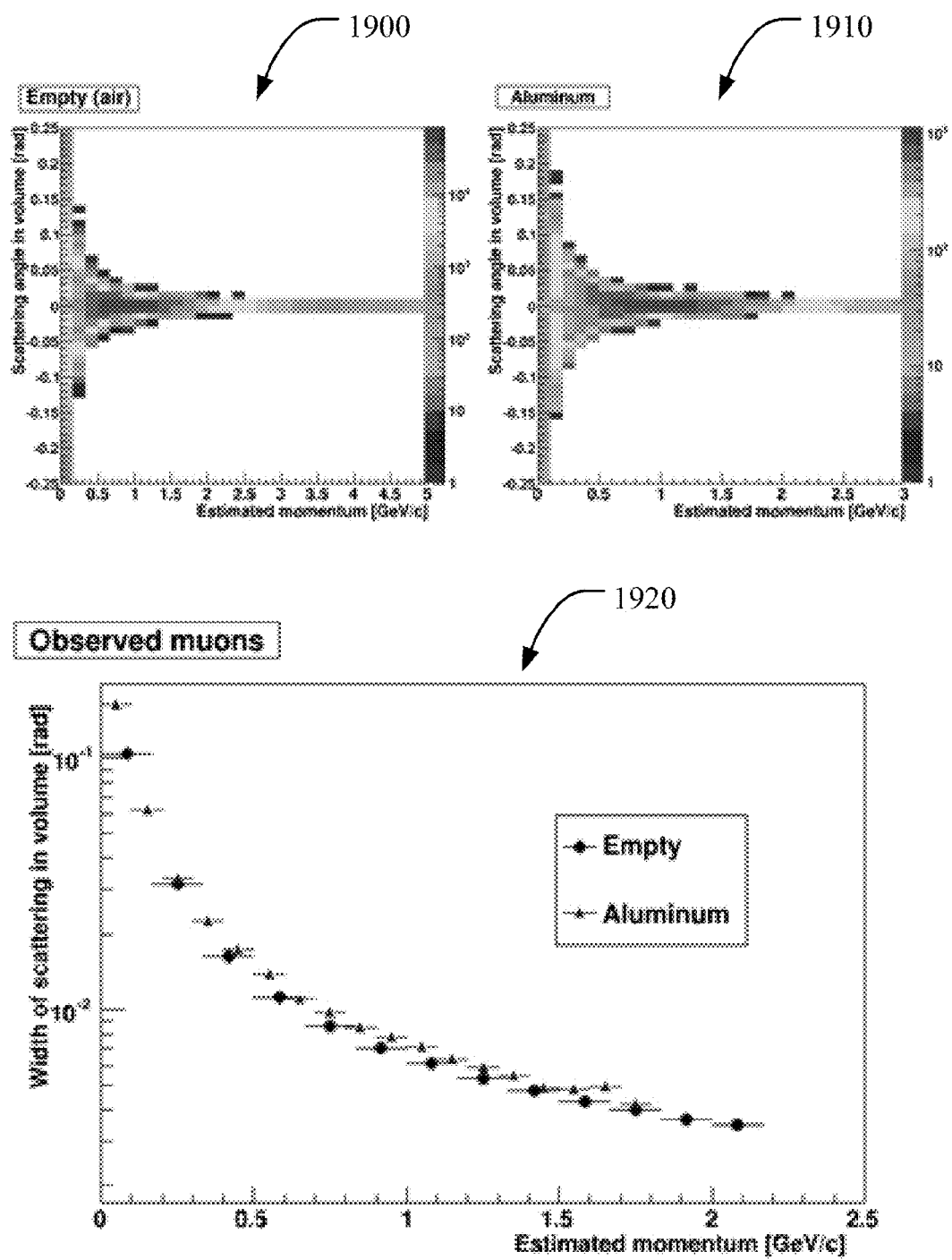
FIG. 19 shows the scattering angle inside the scanner volume for muons passing through air (top left) and a block of aluminum (top right) in the PSDV is plotted against the estimated momentum.

While FIG. 14 shows how the muon's scattering inside the SuperModules is related to its momentum, FIG. 19 shows the same inverse relationship to width of scattering holds true for scattering measured in the scanner volume. FIG. 19 shows the scattering angle inside the scanner volume for muons passing through air (top left 1900) and a block of aluminum (top right 1910) in the PSDV is plotted against the estimated momentum. The extra scattering material provided by the aluminum is reflected in the greater scattering width of the muons passing through the aluminum (top 1900 and 1910). A muon is expected to scatter more when it passes through material of greater radiation length, such as the block of aluminum, compared to the same volume of air. This behavior is seen in the muons observed with the PSDV (FIG. 19, 1920). Of the data analyzed, muons passing through the steel and lead block also show more scattering than air, but comparable to aluminum despite being of larger radiation lengths in thickness. It is possible that the surface areas of the blocks are not large enough to obtain reliable or sufficient muon sample.

Some MT reconstruction studies published to date assume full knowledge of the simulated muon momentum or assume a constant nominal momentum. For our MMPDS, the momentum of each observed cosmic ray muon is not known, so we need to be able to estimate the muon's momentum with a reasonable resolution. With less than 60% of error in momentum estimate for most muons, based on comparison to simulation, this method is a significant step in that direction; however, additional work to improve the detector's measurement resolution, as well as refine the method itself is still needed and will be ongoing.

Additional data, especially with simple materials with constant thickness over a large surface area can improve the measurement of scattering inside the scanner volume as a function of the estimated momentum.

In some implementation, the method can be applied to stopped tracks, i.e., particles that are completely absorbed inside the scanner volume and do not penetrate the volume to the lower SuperModule.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments Only a few implementations and examples are described and other implementations, enhancements and variations can be made based on what is described and illustrated in this patent document.

What is claimed is:

1. A method for measuring momentum of charged particles from charged particle tomographic data, the method comprising:
    obtaining charged particle tomographic data corresponding to scattering angles of charged particles passing through an object volume at one or more charged particle position detectors;
    determining a distribution of scattering angles associated with the charged particles, using measured data collected from the one or more position detectors, based on deviations of local trajectories of the charged particles in one or more planes relative to a reference trajectory;
    determining a length of the scattering material based on the characteristics of the one or more position detectors and the charged particles' angle of incidence on the one or more position detectors; and
    obtaining charged particle momentum estimates based on the determined distribution of scattering angles and the length of the scattering material.

2. The method of claim 1, wherein the charged particle momentum estimates are used to determine a reconstructed object volume scattering density using the scattering angles.

3. The method of claim 1, wherein the reference trajectory is an average of all local trajectories obtained from data collected from at least two layers of the position detectors.

4. The method of claim 1, further comprising combining multiple local trajectories to form a non-linear particle path through multiple layers of the position detectors.

5. The method of claim 1, wherein the one or more position detectors include a drift tube.

6. The method of claim 1, wherein a local trajectory of the charged particles is at an arbitrary direction in a 3-dimensional coordinate system, and the one or more planes include a plane in the 3-dimensional coordinate system.

7. The method of claim 1, wherein the distribution of scattering angles is determined based on a distribution, $\sigma_\theta^{plane}$, of scattering angles in a plane that is related to a three-dimensional scattering angle distribution, $\sigma_\theta^{3D}$, based on the following relationship: $\sigma_\theta^{3D} = \sqrt{2}\sigma_\theta^{plane}$.

8. The method of claim 1, wherein the distribution of scattering angles is determined based on the distribution of the local trajectories as the root mean square (RMS) of all the scattering angles for a given charged particle.

9. The method of claim 1, wherein the one or more position detectors include a drift tube and the characteristics of the one or more position detectors include an inner radius of the drift tube and a wall thickness of the drift tube.

10. The method of claim 9, wherein determining the length of the scattering material is further based on the charged particle(s) incident angle projected along a direction of the drift tube's length.

11. The method of claim 9, wherein the length of the scattering material is determined according to the following equation:

$$L = \sum_i^{tubes} \left( \frac{2 \cdot \left( \sqrt{(R_{inner} - t)^2 - (r_{drift}^i)^2} - \sqrt{R_{inner}^2 - (r_{drift}^i)^2} \right)}{\cos(\alpha_{\|,incoming})} \right),$$

wherein t is the wall thickness of the drift tube, $r_{drift}$ is the drift radius, $\alpha_{\|,incoming}$ is the charged particle(s) incident angle projected along the drift tube's length, and $R_{inner}$ is the drift tube's inner radius.

12. The method of claim 1, wherein the charged particle momentum estimates is obtained according the following equation:

$$p = f \cdot \frac{13.6 \text{ MeV}}{\sqrt{2}\, \sigma_\theta^{plane}\, c} \sqrt{L/X_0}\, [1 + 0.038\, \ln(L/X_0)],$$

wherein f is an empirical proportional factor, L is the length of the scattering material, $X_0$ is the radiation length of the scattering material, c is the speed of light, and $\sigma^{74}{}_{plane}$ is a distribution of scattering angles in a plane.

13. The method of claim 1, further comprising outputting the reconstructed object volume scattering density for presentation on a display.

14. A computer program product, embodied on a non-transitory computer readable medium, the computer program product comprising:
program code for obtaining charged particle tomographic data corresponding to scattering angles of charged particles passing through an object volume at one or more charged particle position detectors;
program code for determining a distribution of scattering angles associated with the charged particles, using measured data collected from the one or more position detectors, based on deviations of local trajectories of the charged particles in one or more planes relative to a reference trajectory;
program code for determining a length of the scattering material based on the characteristics of the one or more position detectors and the charged particles' angle of incidence on the one or more position detectors; and
program code for obtaining charged particle momentum estimates based on the determined distribution of scattering angles and the length of the scattering material.

15. The computer program product of claim 14, wherein the charged particle momentum estimates are used to determine a reconstructed object volume scattering density using the scattering angles.

16. A device, comprising:
a processor comprising electronic circuits; and
a memory comprising processor executable code, the processor executable code, when executed by the process configures the device to:
obtain charged particle tomographic data corresponding to scattering angles of charged particles passing through an object volume at one or more charged particle position detectors;
determine a distribution of scattering angles associated with the charged particles, using measured data collected from the one or more position detectors, based on deviations of local trajectories of the charged particles in one or more planes relative to a reference trajectory;
determine a length of the scattering material based on the characteristics of the one or more position detectors and the charged particles' angle of incidence on the one or more position detectors; and
obtain charged particle momentum estimates based on the determined distribution of scattering angles and the length of the scattering material.

17. The device of claim 16, wherein the charged particle momentum estimates are used to determine a reconstructed object volume scattering density using the scattering angles.

18. A system for measuring momentum of charged particles from charged particle tomographic data, comprising:
a first set of position detector located on a first side of an object volume to measure positions and angles of incident charged particles towards the object volume;
a second set of position sensitive detectors located on a second side of the object volume to measure positions and angles of outgoing charged particles exiting the object volume; and
a signal processing unit coupled to the first set of position detectors and to the second set of position detectors to receive data of measured signals from the first set of position detectors and measured signals from the second set of position detectors, the signal processing unit to:
determine a distribution of scattering angles associated with the charged particles, using measured data collected from the one or more position detectors, based on deviations of local trajectories of the charged particles in one or more planes relative to a reference trajectory;
determine a length of the scattering material based on the characteristics of the first or the second set of position detectors and the charged particles' angle of incidence on the first or the second set of position detectors; and
obtain charged particle momentum estimates based on the determined distribution of scattering angles and the length of the scattering material.

19. The system of claim 18, wherein the signal processing unit further determines a reconstructed object volume scattering density based on the charged particle momentum estimates and the scattering angles.

20. The system of claim 19, further comprising a display coupled to the signal processing unit to receive and display data representing the reconstructed object volume scattering density.

21. The system of claim 18, wherein the reference trajectory is an average of all local trajectories obtained from data collected from at least two layers of the position detectors.

22. The system of claim 18, wherein the processing unit further combines multiple local trajectories to form a non-linear particle path through multiple layers of the position detectors.

23. The system of claim 18, wherein the first or the second set of position detectors include a drift tube.

24. The system of claim 18, wherein a local trajectory of the charged particles is at an arbitrary direction in a 3-dimensional coordinate system, and the one or more planes include a plane in the 3-dimensional coordinate system.

25. The system of claim 18, wherein the processing unit determines the distribution of scattering angles based on a distribution, $\sigma_\theta^{plane}$, of scattering angles in a plane that is related to a three-dimensional scattering angle distribution, $\sigma_\theta^{3D}$, based on the following relationship: $\sigma_\theta^{3D} = \sqrt{2}\sigma_\theta^{plane}$.

26. The system of claim 18, wherein the processing unit determines the distribution of scattering angles based on the distribution of the local trajectories as the root mean square (RMS) of all the scattering angles for a given charged particle.

27. The system of claim 18, wherein the first or the second set of position detectors include a drift tube and the characteristics of the first or the second set of position detectors include an inner radius of the drift tube and a wall thickness of the drift tube.

28. The system of claim 27, wherein the processing unit determines the length of the scattering material based on the charged particle(s) incident angle projected along a direction of the drift tube's length.

29. The system of claim 27, wherein the length of the scattering material is determined according to the following equation:

$$L = \sum_i^{tubes} \left( \frac{2 \cdot \left( \sqrt{(R_{inner} - t)^2 - (r_{drift}^i)^2} - \sqrt{R_{inner}^2 - (r_{drift}^i)^2} \right)}{\cos(\alpha_{\|,incoming})} \right),$$

wherein t is the wall thickness of the drift tube, $r_{drift}$ is the drift radius, $\alpha_{\|,incoming}$ is the charged particle(s) incident angle projected along the drift tube's length, and $R_{inner}$ is the drift tube's inner radius.

30. The system of claim 18, wherein the charged particle momentum estimates is obtained according the following equation:

$$p = f \cdot \frac{13.6 \text{ MeV}}{\sqrt{2}\, \sigma_\theta^{plane} c} \sqrt{L/X_0}\, [1 + 0.038\, \ln(L/X_0)],$$

wherein f is an empirical proportional factor, L is the length of the scattering material, $X_0$ is the radiation length of the scattering material, c is the speed of light, and $\sigma_\theta^{plane}$ is a distribution of scattering angles in a plane.

* * * * *

UNITED STATES PATENT AND TRADEMARK OFFICE
CERTIFICATE OF CORRECTION

PATENT NO. : 9,588,064 B2  
APPLICATION NO. : 14/874305  
DATED : March 7, 2017  
INVENTOR(S) : Priscilla Kurnadi, Thomas Taylor and Sean Simon Page 1 of 1

It is certified that error appears in the above-identified patent and that said Letters Patent is hereby corrected as shown below:

In the Drawings

In Fig. 1, Sheet 1 of 19, delete "  " and insert -- 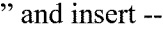 --, therefor.

In the Claims

In Column 18, Line 66, in Claim 12, delete "$\sigma^{74}\ plane$" and insert -- $\sigma_\theta^{plane}$ --, therefor.

Signed and Sealed this  
Twenty-fourth Day of December, 2019

Andrei Iancu  
*Director of the United States Patent and Trademark Office*